US008329795B2

(12) United States Patent
Dakka et al.

(10) Patent No.: US 8,329,795 B2
(45) Date of Patent: Dec. 11, 2012

(54) OIL BASED POLYOLS OR DIACIDS ESTERIFIED WITH OXO-ACIDS OR OXO-ALCOHOLS FOR PRODUCING PLASTICIZERS

(75) Inventors: Jihad Mohammed Dakka, Whitehouse Station, NJ (US); Edmund John Mozeleski, Califon, NJ (US); Lisa Saunders Baugh, Ringoes, NJ (US); Allen David Godwin, Seabrook, TX (US); Diana S. Smirnova, High Bridge, NJ (US)

(73) Assignee: ExxonMobil Research And Engineering Company, Annandale, NJ (US)

( * ) Notice: Subject to any disclaimer, the term of this patent is extended or adjusted under 35 U.S.C. 154(b) by 57 days.

(21) Appl. No.: 12/830,606

(22) Filed: Jul. 6, 2010

(65) Prior Publication Data

US 2011/0009548 A1 Jan. 13, 2011

Related U.S. Application Data

(60) Provisional application No. 61/270,350, filed on Jul. 7, 2009.

(51) Int. Cl.
*C08K 5/00* (2006.01)
(52) U.S. Cl. ........................ 524/287; 524/285
(58) Field of Classification Search ............ 524/287
See application file for complete search history.

(56) References Cited

U.S. PATENT DOCUMENTS

| 2,360,555 A | 10/1944 | Evans et al. |
| 2,438,041 A | 3/1948 | Dutcher |
| 2,476,252 A | 7/1949 | Thomas et al. |
| 2,817,673 A | 12/1957 | Roelen et al. |
| 2,841,614 A | 7/1958 | Buchner et al. |
| 4,390,717 A | 6/1983 | Ishikawa et al. |
| 4,524,213 A | 6/1985 | Suzuki et al. |
| 4,528,396 A | 7/1985 | Sanderson et al. |
| 5,026,756 A | 6/1991 | Arendt |
| 6,274,756 B1 | 8/2001 | Caers et al. |
| 6,482,972 B1 | 11/2002 | Bahrmann et al. |
| 6,740,254 B2 | 5/2004 | Zhou et al. |
| 6,777,514 B2 | 8/2004 | Patil et al. |
| 7,145,042 B2 | 12/2006 | Volland et al. |
| 7,297,738 B2 | 11/2007 | Gosse et al. |
| 2003/0171604 A1 | 9/2003 | Mizuno et al. |
| 2006/0247461 A1 | 11/2006 | Schlosberg et al. |
| 2008/0242895 A1 | 10/2008 | Godwin et al. |

FOREIGN PATENT DOCUMENTS

| GB | 786948 | * 11/1957 |
| JP | 2001-207002 | 7/2001 |
| WO | 9932427 | 12/1998 |
| WO | 03/029339 | 4/2003 |
| WO | 2004/046078 | 6/2004 |
| WO | 2009/118261 | 10/2009 |

OTHER PUBLICATIONS

Co-pending commonly owned U.S. Appl. No. 61/040,480.
Co-pending commonly owned U.S. Appl. No. 12/653,744.
A. D. Godwin, "Plasticizers", Applied Polymer Science 21st Century, edited by C. D. Craver and C. E. Carraher, Elsevier (2000), pp. 157-175.

* cited by examiner

*Primary Examiner* — Hui Chin
(74) *Attorney, Agent, or Firm* — Robert A. Migliorini

(57) ABSTRACT

Oxo-diesters of cyclic olefins, methods of making them and their use as plasticizers in polymer compositions are disclosed.

6 Claims, 3 Drawing Sheets

DINP (left 4 bars)   1   2*   4   5   6   7   8   DINP   10

OIL BASED POLYOLS OR DIACIDS ESTERIFIED WITH OXO-ACIDS OR OXO-ALCOHOLS FOR PRODUCING PLASTICIZERS

CROSS-REFERENCE TO RELATED APPLICATIONS

This is a Non-Provisional Application that claims priority to U.S. Provisional Application No. 61/270,350 filed on Jul. 7, 2009 and herein incorporated by reference herein in its entirety.

FIELD

This disclosure relates to oxo-diesters useful as non-phthalate plasticizers and for a wide range of polymer resins and methods of making such plasticizers.

BACKGROUND

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Plasticizers can be characterized on the basis of their chemical structure. The most important chemical class of plasticizers is phthalic acid esters, which accounted for about 85% worldwide of PVC plasticizer usage in 2002. However, in the recent past there has been an effort to decrease the use of phthalate esters as plasticizers in PVC, particularly in end uses where the product contacts food, such as bottle cap liners and sealants, medical and food films, or for medical examination gloves, blood bags, and IV delivery systems, flexible tubing, or for toys, and the like. For these and most other uses of plasticized polymer systems, however, a successful substitute for phthalate esters has heretofore not materialized.

One such suggested substitute for phthalates are esters based on cyclohexanoic acid. In the late 1990's and early 2000's, various compositions based on cyclohexanoate, cyclohexanedioates, and cyclohexanepolyoate esters were said to be useful for a range of goods from semi-rigid to highly flexible materials. See, for instance, WO 99/32427, WO 2004/046078, WO 2003/029339, WO 2004/046078, U.S. Application No. 2006-0247461, and U.S. Pat. No. 7,297,738.

Other suggested substitutes include esters based on benzoic acid (see, for instance, U.S. Pat. No. 6,740,254, and also PCT Publication No. WO2009/118261A1, and polyketones, such as described in 6,777,514; and also co-pending, commonly-assigned, U.S. Patent Publication No. 2008-0242895. Epoxidized soybean oil, which has much longer alkyl groups ($C_{16}$ to $C_{18}$) has been tried as a plasticizer, but is generally used as a PVC stabilizer. Stabilizers are used in much lower concentrations than plasticizers. Copending and commonly assigned U.S. Patent Publication No. US 2010-0159177 discloses triglycerides with a total carbon number of the triester groups between 20 and 25, produced by esterification of glycerol with a combination of acids derived from the hydroformylation and subsequent oxidation of $C_3$ to $C_9$ olefins, having excellent compatibility with a wide variety of resins and that can be made with a high throughput.

U.S. Pat. No. 2,476,252 discloses di-ester reaction products of styrene epoxide with carboxylic acids having 3 to 11 carbon atoms which find use as plasticizers for natural or synthetic resins.

U.S. Pat. No. 2,817,673 discloses esters of dicyclopentadiene, wherein dicyclopentadiene is hydroformylated in the presence of water gas ($H_2$/CO) to form dicyclodecane-dimethylal, which is further converted to dicyclodecane-dimethylol, then to the corresponding dicarboxylic acid, and subsequently esterified with lower alcohols. The esters so-formed are disclosed to be useful as softeners and as high grade lubricating oils.

U.S. Pat. No. 4,390,717 discloses a process for preparing mono- or di-carboxylic acid esters of dicyclopentadiene by reacting the dicyclopentadiene with carbon monoxide and an alcohol in the presence of a cobalt catalyst. The cycloaliphatic carboxylates so-formed can be used as a plasticizer or lubricant.

U.S. Pat. No. 4,528,396 discloses dicyclopentadiene-derived ester compounds useful as plasticizers, lubricants, solvents and fuel additives.

Japanese Patent Application Publication Number P 2001-207002 describes 1,2-dicarboxylic acid esters of cyclohexane derived from mixtures containing from 80 to 97 wt % of $C_9$ branched alcohols. JP 2001-207002 compares, as plasticizers, these esters with dioctyl phthalate and finds improved cold resistance, viscosity and viscosity stability over time.

U.S. Pat. No. 7,297,738, incorporated herein by reference in its entirety, discloses esters of cyclohexane polycarboxylic acids which are used as plasticizers for polyvinyl chloride. However, only 1,2-diesters of cyclohexane are disclosed.

Thus what is needed is a method of making a general purpose non-phthalate plasticizer having and providing a plasticizer having suitable melting or chemical and thermal stability, pour point, glass transition, increased compatibility, good performance and low temperature properties.

SUMMARY

In one aspect, the present application is directed to oxo-diesters of cyclohexane (Ia)-(Id):

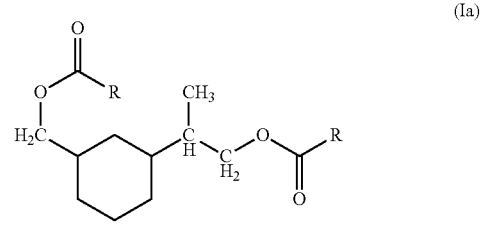

(Ia)

-continued (Ib)
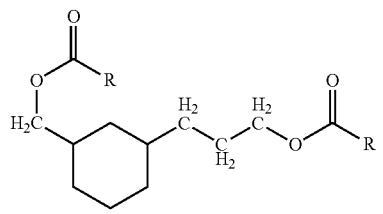

(Ic)
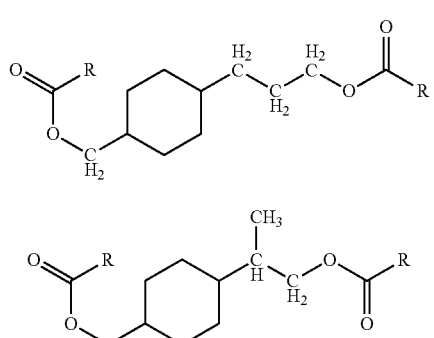

(Id)
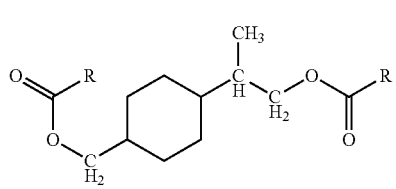

or combinations thereof, wherein each R is the same or different and represents a $C_5$-$C_8$ alkyl group, or mixtures of $C_5$-$C_8$ alkyl groups.

In another embodiment, the present application is directed to oxo-diesters of cyclohexane of the formula (IIa)-(IId):

(IIa)
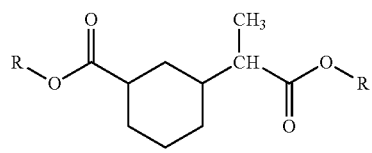

(IIb)
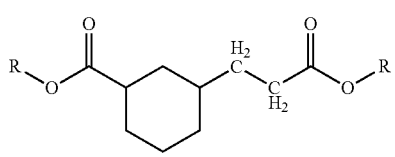

(IIc)
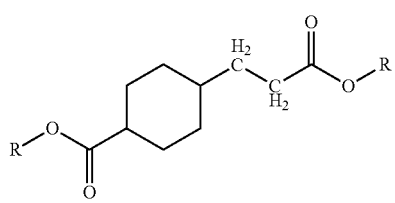

(IId)
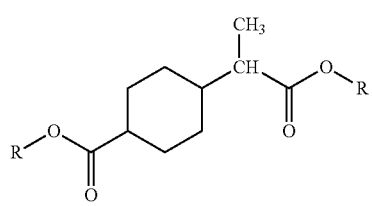

or combinations thereof, wherein each R is the same or different and represents a $C_6$-$C_9$ alkyl group, or mixtures of $C_6$-$C_9$ alkyl groups.

In another embodiment, the present application is directed to a process for making oxo-diesters of cyclohexane of the formula (Ia)-(Id), (Ia)
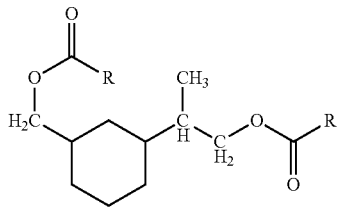

(Ib)
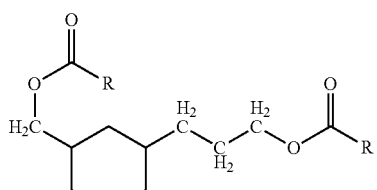

(Ic)
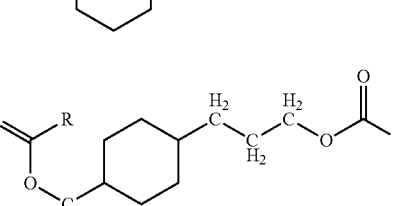

(Id)
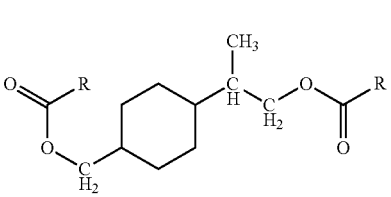

or combinations thereof, wherein each R is the same or different and represents a $C_5$-$C_8$ alkyl group, or mixtures of $C_5$-$C_8$ alkyl groups, by dimerizing 1,3-butadiene to form 4-ethenyl-cyclohexene; hydroformylating said 4-ethenyl-cyclohexene to form a dialdehyde of cyclohexane or mixture of dialdehydes of the formula (IIIa)-(IIId);

(IIIa)
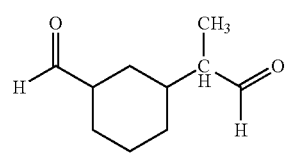

(IIIb)
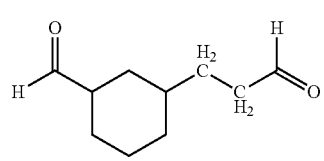

(IIIc)
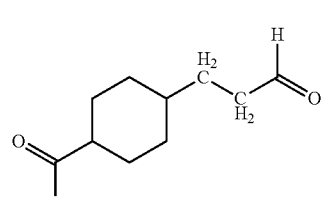

(IIId)

[Structure IIId: cyclohexane with -CH(CH₃)-CHO and -CHO substituents]

hydrogenating said dialdehyde or mixture of dialdehydes to form the corresponding dialcohol of cyclohexane or mixture of dialcohols; and esterifying said dialcohol of cyclohexane or mixture of dialcohols with $C_6$-$C_9$ oxo-acids.

In another embodiment, the present application is directed to a process for making oxo-diesters of cyclohexane of the formula (IIa)-(IId):

(IIa)

[Structure IIa]

(IIb)

[Structure IIb]

(IIc)

[Structure IIc]

(IId)

[Structure IId]

or combinations thereof, wherein each R is the same or different and represents a $C_6$-$C_9$ alkyl group, or mixtures of $C_6$-$C_9$ alkyl groups, by dimerizing 1,3-butadiene to form 4-ethenyl-cyclohexene; hydroformylating said 4-ethenyl-cyclohexene to form a dialdehyde of cyclohexane or mixtures of dialdehydes of the formula (IIIa)-(IIId);

(IIIa)

[Structure IIIa]

(IIIb)

[Structure IIIb]

(IIIc)

[Structure IIIc]

(IIId)

[Structure IIId]

oxidizing said dialdehyde or mixture of dialdehydes to form the corresponding diacid of cyclohexane or mixture of diacids; and esterifying said diacid of cyclohexane or mixture of diacids with $C_6$-$C_9$ oxo-alcohols.

In another embodiment, the present application is directed to a process for making oxo-diesters of a saturated ring compound, by providing a di-olefin of the formula (IV):

(IV)

[Structure IV: cyclohexene with R₁, R₂, R₃, R₄ substituents]

wherein $R^1$ and $R^2$ each of which can be hydrogen, or can be joined to form a single methylene group, —$CH_2$— and $R^3$ and $R^4$, wherein one is hydrogen and the other is —CH=$CH_2$, or can be joined to form —$CH_2$—CH=CH—, and if both $R^1$ and $R^2$ are hydrogen then one of $R^3$ or $R^4$ is —CH=$CH_2$; hydroformylating said di-olefin to form a dialdehyde; oxidizing or hydrogenating said dialdehyde to form the corresponding diacid or dialcohol; and esterifying said diacid or dialcohol with either $C_6$-$C_9$ oxo-alcohols or $C_6$-$C_9$ oxo-acids, respectively.

Conveniently, the process can be conducted wherein said di-olefin is 4-ethenyl-cyclohexene and said oxo-diester is selected from the group consisting of:

(IIa)

[Structure IIa]

-continued

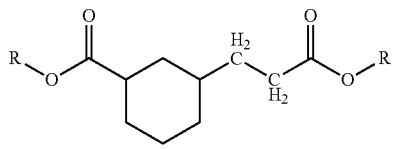
(IIb)

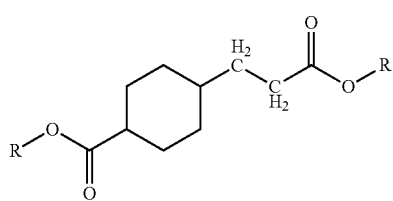
(IIc)

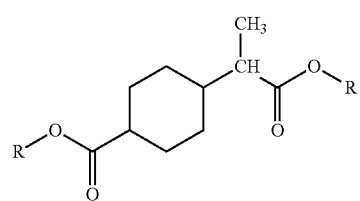
(IId)

and combinations thereof, wherein each R is the same or different and represents a $C_6$-$C_9$ alkyl group, or mixtures of $C_6$-$C_9$ alkyl groups; and

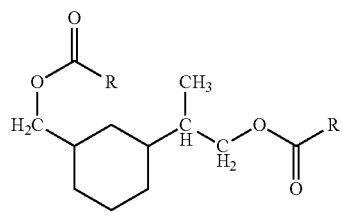
(Ia)

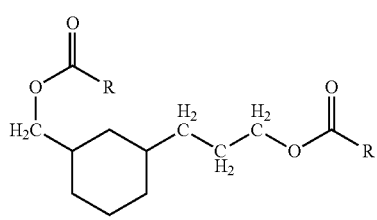
(Ib)

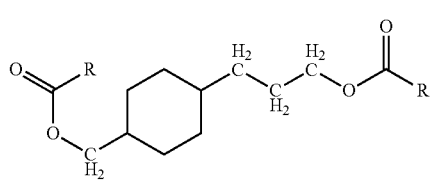
(Ic)

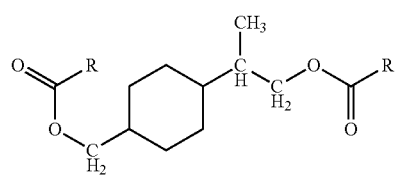
(Id)

and combinations thereof, wherein each R is the same or different and represents a $C_5$-$C_8$ alkyl group, or mixtures of $C_5$-$C_8$ alkyl groups.

In another embodiment, the present disclosure is directed to oxo-diesters of dicyclopentadiene of the formulas (Va)-(Vd):

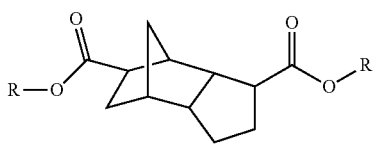
(Va)

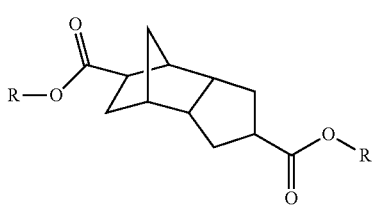
(Vb)

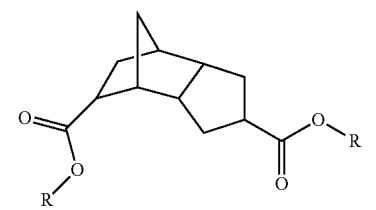
(Vc)

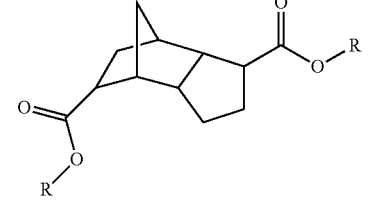
(Vd)

or combinations thereof, wherein each R is the same or different and represents a $C_6$-$C_9$ alkyl group, or mixtures of $C_6$-$C_9$ alkyl groups.

In another embodiment, the present disclosure is directed to oxo-diesters of dicyclopentadiene of the formulas (VIa)-(VId):

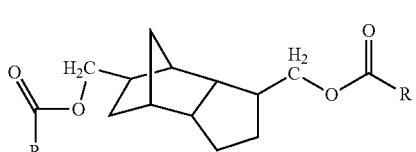
(VIa)

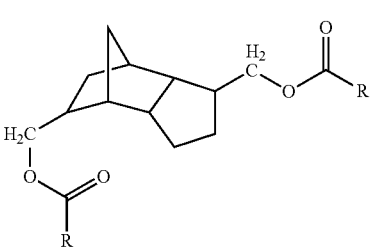
(VIb)

-continued

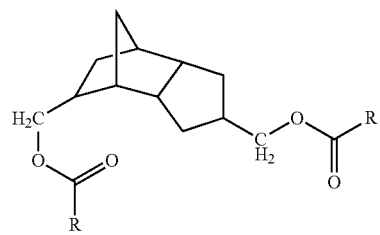
(VIc)

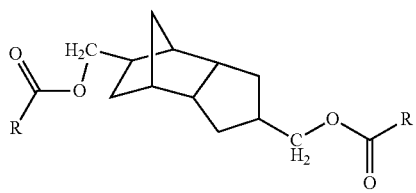
(VId)

or combinations thereof, wherein each R is the same or different and represents a $C_5$-$C_8$ alkyl group, or mixtures of $C_5$-$C_8$ alkyl groups.

Another embodiment of the present disclosure is directed to a process of making oxo-diesters of dicyclopentadiene of the formulas (Va)-(Vd):

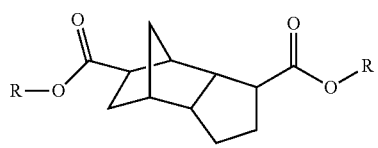
(Va)

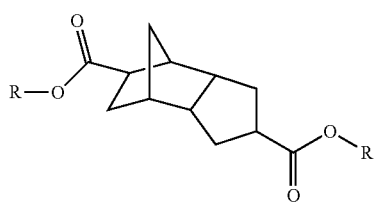
(Vb)

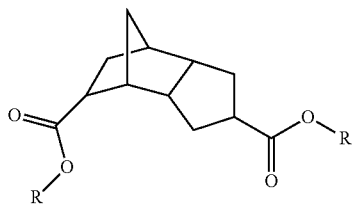
(Vc)

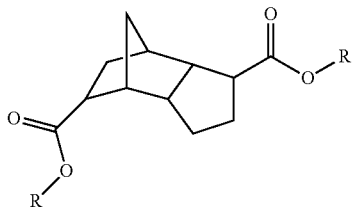
(Vd)

or combinations thereof, wherein each R is the same or different and represents a $C_6$-$C_9$ alkyl group, or mixtures of $C_6$-$C_9$ alkyl groups, comprising hydroformylating dicyclopentadiene to form a dialdehyde or mixtures of dialdehydes of dicyclopentadiene; oxidizing said dialdehyde or mixture of dialdehydes to form the corresponding diacid of dicyclopentadiene; and esterifying said diacid with $C_6$-$C_9$ oxo-alcohols.

Another embodiment of the present disclosure is directed to a process of making oxo-diesters of dicyclopentadiene of the formulas (VIa)-(VId):

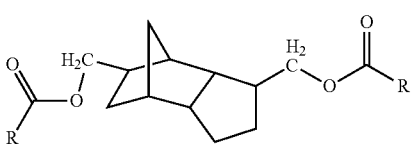
(VIa)

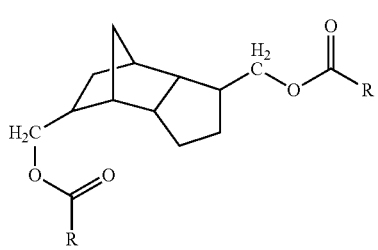
(VIb)

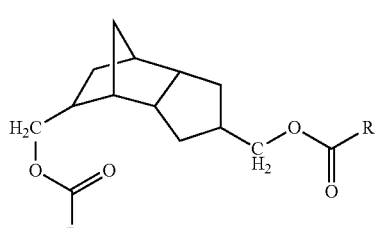
(VIc)

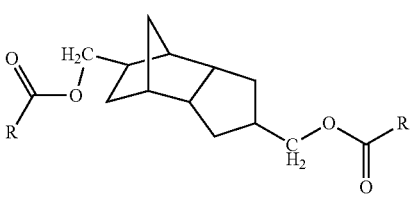
(VId)

or combinations thereof, wherein each R is the same or different and represents a $C_5$-$C_8$ alkyl group, or mixtures of $C_5$-$C_8$ alkyl groups, comprising hydroformylating dicyclopentadiene to form a dialdehyde or mixtures of dialdehydes of dicyclopentadiene; hydrogenating said dialdehyde or mixture of dialdehydes to form the corresponding dialcohol of dicyclopentadiene; and esterifying said dialcohol with $C_6$-$C_9$ oxo-acids.

In another embodiment, the present application is directed to a process for making an oxo-diester of the formula

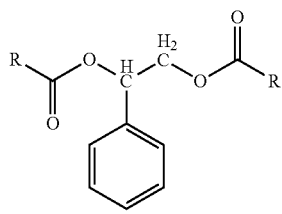
(VII)

wherein each R is the same or different and represents a $C_5$-$C_8$ alkyl group, or mixtures of $C_5$-$C_8$ alkyl groups, by dimerizing 1,3-butadiene to form 4-ethenyl-cyclohexene; dehydrogenating said 4-ethenyl-cyclohexene to form styrene; oxidizing said styrene to form styrene epoxide; optionally hydrolyzing said styrene epoxide to form phenyl-1,2-ethanediol; and esterifying either of said styrene epoxide or phenyl-1,2-ethanediol with a $C_6$-$C_9$ oxo-acid.

In another embodiment, the present application is directed to a polymer composition, comprising a polymer and an oxo-diester of cyclohexane as a plasticizer.

Conveniently, the polymer composition can be formulated such that said plasticizer is an oxo-diester of the formula (Ia)-(Id):

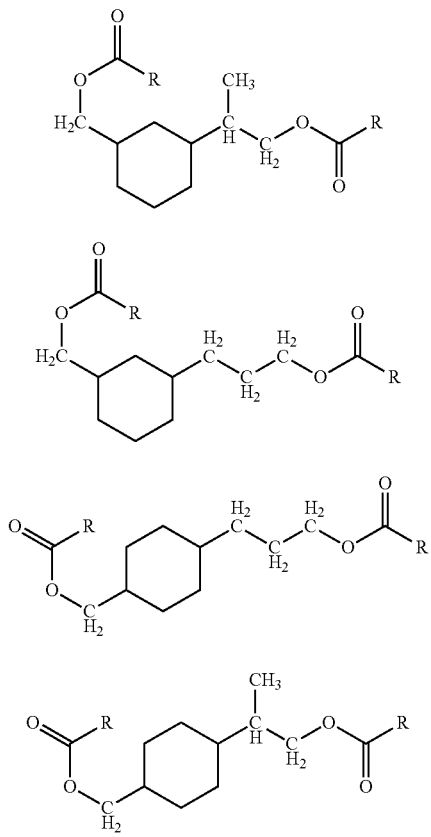

or combinations thereof, wherein each R is the same or different and represents a $C_5$-$C_8$ alkyl group, or mixtures of $C_5$-$C_8$ alkyl groups.

Alternatively, the polymer composition can be formulated such that said plasticizer is an oxo-diester of the formula (IIa)-(IId):

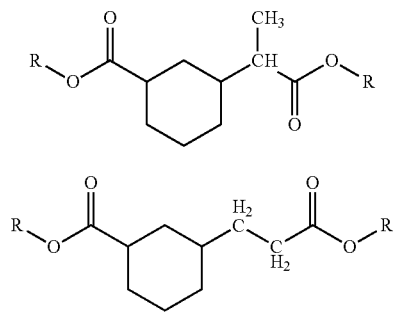

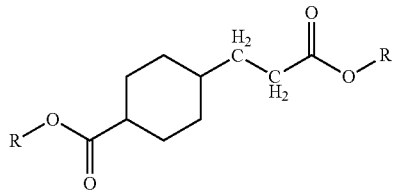

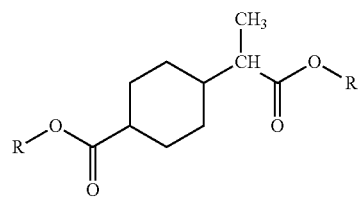

or combinations thereof, wherein each R is the same or different and represents a $C_6$-$C_9$ alkyl group, or mixtures of $C_6$-$C_9$ alkyl groups.

Conveniently, the polymer composition can be formulated such that the polymer is selected from the group consisting of vinyl chloride resins, polyesters, polyurethanes, ethylene-vinyl acetate copolymers, rubbers, poly(meth)acrylics and mixtures thereof.

Conveniently, the polymer composition can be formulated such that the polymer is polyvinylchloride.

In another embodiment, the present application is directed to a polymer composition, comprising a polymer and an oxo-diester of dicyclopentadiene as a plasticizer.

Conveniently, the polymer composition can be formulated such that said plasticizer is an oxo-diester of the formula (Va)-(Vd):

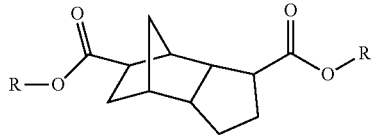

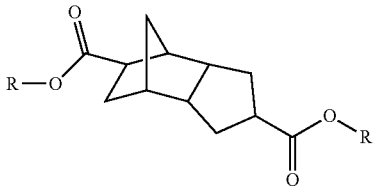

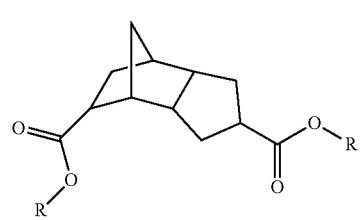

-continued

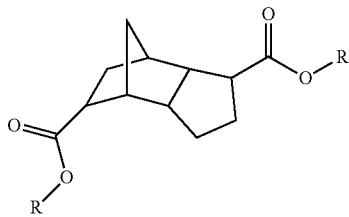
(Vd)

or combinations thereof, wherein each R is the same or different and represents a $C_6$-$C_9$ alkyl group, or mixtures of $C_6$-$C_9$ alkyl groups.

Alternatively, the polymer composition can be formulated such that said plasticizer is a oxo-diester of the of the formula (VIa)-(VId):

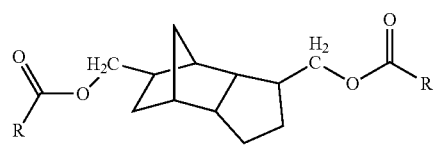
(VIa)

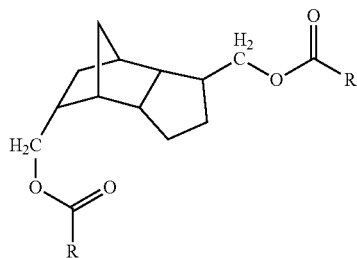
(VIb)

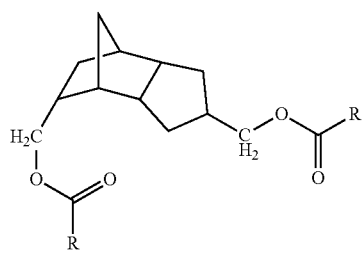
(VIc)

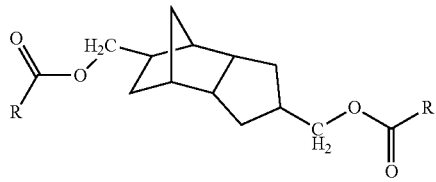
(VId)

or combinations thereof, wherein each R is the same or different and represents a $C_5$-$C_8$ alkyl group, or mixtures of $C_5$-$C_8$ alkyl groups.

Conveniently, the polymer composition can be formulated such that said polymer is selected from the group consisting of vinyl chloride resins, polyesters, polyurethanes, ethylene-vinyl acetate copolymers, rubbers, poly(meth)acrylics and mixtures thereof.

Conveniently, the polymer composition can be formulated such that said polymer is polyvinylchloride.

In another embodiment, the present application is directed to a polymer composition, comprising a polymer and an oxo-diester of phenyl-1,2-ethanediol as a plasticizer.

Conveniently, the polymer composition can be formulated such that the plasticizer is an oxo-diester of the formula:

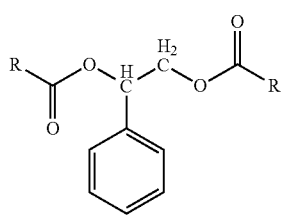
(VII)

wherein each R is the same or different and represents a $C_5$-$C_8$ alkyl group, or mixtures of $C_5$-$C_8$ alkyl groups.

Conveniently, the polymer composition can be formulated such that the polymer is selected from the group consisting of vinyl chloride resins, polyesters, polyurethanes, ethylene-vinyl acetate copolymers, rubbers, poly(meth)acrylics and mixtures thereof.

Conveniently, the polymer composition can be formulated such that the polymer is polyvinylchloride.

In another embodiment, the present disclosure is directed to vicinal oxo-diesters of dicyclopentadiene of the following formulas:

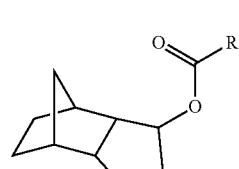
(VIII)

or
(IX)

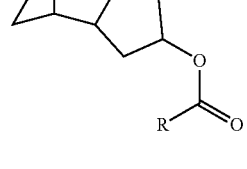

or combinations thereof, wherein each R is the same or different and represents a $C_5$-$C_8$ alkyl group, or mixtures of $C_5$-$C_8$ alkyl groups.

In another embodiment, the present application is directed to a process for making vicinal oxo-diesters of dicyclopentadiene of the formulas:

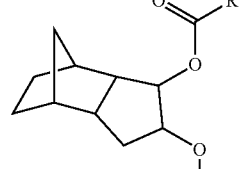
(VIII)

or

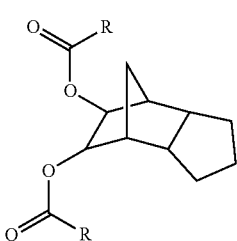

(IX)

or combinations thereof, wherein each R is the same or different and represents a $C_5$-$C_8$ alkyl group, or mixtures of $C_5$-$C_8$ alkyl groups, by selective hydrogenation of dicyclopentadiene to a monoolefin; epoxidation of the monoolefin to form an epoxide; optionally hydrolyzing said epoxide to form a diol; and esterifying either of said epoxide or diol with a $C_6$-$C_9$ oxo-acid.

In another embodiment, the present application is directed to a polymer composition, comprising a polymer and a vicinal oxo-diester of dicyclopentadiene of the formulas:

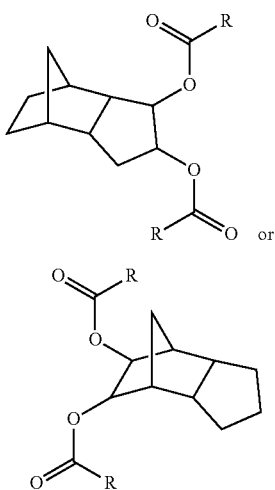

(VIII)

or (IX)

or combinations thereof, wherein each R is the same or different and represents a $C_5$-$C_8$ alkyl group, or mixtures of $C_5$-$C_8$ alkyl groups.

Conveniently, the polymer composition can be formulated such that the polymer is selected from the group consisting of vinyl chloride resins, polyesters, polyurethanes, ethylene-vinyl acetate copolymers, rubbers, poly(meth)acrylics and mixtures thereof.

Conveniently, the polymer composition can be formulated such that the polymer is polyvinylchloride.

In another embodiment, the present application is directed to a process for making an oxo-diester of the formulas:

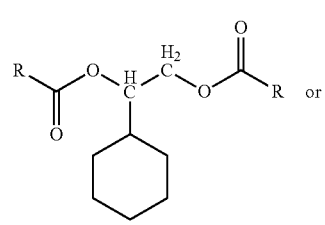

(X)

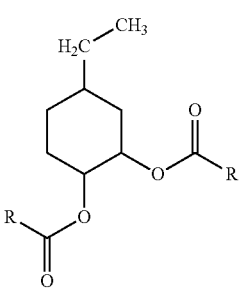

(XI)

or combinations thereof, wherein each R is the same or different and represents a $C_5$-$C_8$ alkyl group, or mixtures of $C_5$-$C_8$ alkyl groups, by selective hydrogenation of 4-ethenyl-cyclohexene to a monoolefin; epoxidation of the monoolefin to form an epoxide; optionally hydrolyzing said epoxide to form a diol; and esterifying either of said epoxide or diol with a $C_6$-$C_9$ oxo-acid.

In another embodiment, the present application is directed to a polymer composition, comprising a polymer and an oxo-diester of the of the formulas:

(X)

or (XI)

or combinations thereof, wherein each R is the same or different and represents a $C_5$-$C_8$ alkyl group, or mixtures of $C_5$-$C_8$ alkyl groups.

Conveniently, the polymer compositions can be formulated such that the polymer is selected from the group consisting of vinyl chloride resins, polyesters, polyurethanes, ethylene-vinyl acetate copolymers, rubbers, poly(meth)acrylics and mixtures thereof.

Conveniently, the polymer compositions can be formulated such that the polymer is polyvinylchloride.

DETAILED DESCRIPTION

Figure 1:
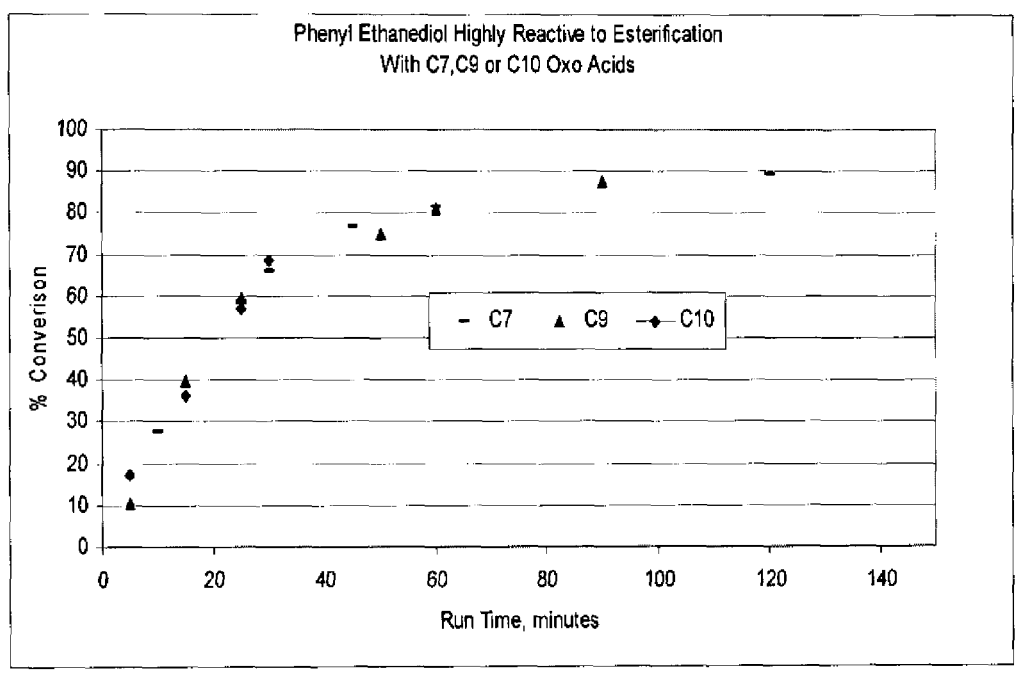
FIG. 1 is a graph indicating the reaction rates of phenyl ethanediol esterification with oxo-$C_7$, $C_9$, and $C_{10}$ acids as described in Examples 1-3.

There is an increased interest in developing new plasticizers that are non-phthalates and which possess good plasticizer performance characteristics but are still competitive economically. The present disclosure is directed towards non-phthalate plasticizers that can be made from low cost feeds and employ fewer manufacturing steps in order to meet economic targets. One route into non-phthalate plasticizers is to produce diols or diacids from higher di-olefin cyclic feeds using hydroformylation, followed by hydrogenation or oxidation. The products of the hydrogenation and the oxidation step(s) are esterified with either oxo-alcohols or oxo-acids to form oxo-esters. Cyclic di-olefin feeds can be made from light cyclic or aliphatic di-olefins, e.g., dimers of butadiene or dicyclopentadiene.

Branched aldehydes can be produced by hydroformylation of $C_5$ to $C_8$ olefins that in turn have been produced by propylene and/or butene oligomerization over solid phosphoric acid or zeolite catalysts. The resulting $C_6$ to $C_9$ aldehydes can then be recovered from the crude hydroformylation product stream by fractionation to remove unreacted olefins. These $C_6$ to $C_9$ aldehydes can then in turn be oxidized to their respective $C_6$ to $C_9$ acids (oxo-acids) using air or enriched air as the oxygen source, or hydrogenated to alcohols (oxo-alcohols). Following the oxidation and the hydrogenation reactions, the $C_6$ to $C_9$ acids and alcohols can then be purified by fractionation to remove unreacted aldehydes and heavies formed during oxidation or hydrogenation. The $C_6$ to $C_9$ acids or alcohols can then be esterified with cyclic di-alcohols or di-acids. Single carbon number acids or alcohols can be used in the esterification, or differing carbon numbers can be use to optimize product cost and performance requirements. The $C_6$ to $C_9$ oxo-acids or oxo-alcohols have an average branching of from about 0.2 to about 3.0 branches per molecule. Average branching is determined by NMR. The average branching of the alkyl groups incorporated into the esters as the residues of the acid or alcohol reagents ranges from about 0.2 to about 3.0 branches per residue.

Described herein is a process for producing new plasticizers suitable for replacing phthalate plasticizers. The new plasticizers are oxo-diesters of various, non-phthalate ring compounds and are produced by hydroformylating di-olefin ring compounds to produce di-aldehydes, which can then be transformed to di-acids or di-alcohols by oxidation or hydrogenation, respectively. Subsequently, the di-acids or di-alcohols are esterified with a corresponding oxo-alcohol or oxo-acid, to form oxo-diester plasticizers.

An "oxo-diester" is a compound having two functional ester moieties within its structure that are derived from esterification of either a di-acid or di-alcohol compound with an oxo-alcohol or oxo-acid, respectively.

An "oxo-alcohol" is an organic alcohol, or mixture of organic alcohols, which is prepared by hydroformylating an olefin, followed by hydrogenation to form the alcohols. Typically, the olefin is formed by light olefin oligomerization over heterogeneous acid catalysts, which olefins are readily available from refinery processing operations. The reaction results in mixtures of longer-chain, branched olefins, which subsequently form longer chain, branched alcohols, as described in U.S. Pat. No. 6,274,756, incorporated herein by reference in its entirety.

An "oxo-acid" is an organic acid, or mixture of organic acids, which is prepared by hydroformylating an olefin, followed by oxidation to form the acids. Typically, the olefin is formed by light olefin oligomerization over heterogeneous acid catalysts, which olefins are readily available from refinery processing operations. The reaction results in mixtures of longer-chain, branched olefins, which subsequently form longer-chain, branched acids.

Alternatively, the oxo-acids or oxo-alcohols can be prepared by aldol condensation of shorter-chain aldehydes to form longer chain aldehydes, as described in U.S. Pat. No. 6,274,756, followed by oxidation or hydrogenation to form the oxo-acids or oxo-alcohols, respectively.

Tables 1 and 2 below provide branching characteristics for typical $C_6$-$C_9$ OXO-alcohols and OXO-acids, measured by $^{13}C$ NMR.

TABLE 1

$^{13}C$ NMR Branching Characteristics of Typical OXO-Alcohols.

| OXO-Alcohol | Avg. Carbon No. | % of α-Carbons w/ Branches[a] | β-Branches per Molecule[b] | Total Methyls per Molecule[c] | Pendant Methyls per Molecule[d] | Pendant Ethyls per Molecule |
|---|---|---|---|---|---|---|
| $C_6$ | — | — | — | — | — | — |
| $C_7$ | 7.3 | 0 | 0.15 | 1.96 | 0.99 | 0.04 |
| $C_8$ | 8.6 | 0 | 0.09 | 3.0 | 1.5 | — |
| $C_9$ | 9.66 | 0 | 0.09 | 3.4 | — | — |

— Data not available.
[a]COH carbon.
[b]Branches at the-CCH$_2$OH carbon.
[c]This value counts all methyl groups, including $C_1$ branches, chain end methyls, and methyl endgroups on $C_2$+ branches.
[d]$C_1$ branches only.

TABLE 2

$^{13}C$ NMR Branching Characteristics of Typical OXO-Acids.

| OXO-Acid | Average Carbon No. | Pendant Methyls[a] | Total Methyls[b] | Pendant Ethyls | % Carbonyls α to Branch[c] |
|---|---|---|---|---|---|
| $C_6$ | — | — | — | — | — |
| $C_7$ | 6.88-7.92 | 0.98-1.27 | 1.94-2.48 | 0.16-0.26 | 11.3-16.4 |
| $C_8$ | 8.1-8.3 | — | 2.7 | — | 12-15 |
| $C_9$ | 9.4 | — | n/a | — | 12 |

— Data not available.
[a]$C_1$ Branches only.
[b]Includes methyls on all branch lengths and chain end methyls.
[c]The "alpha" position in the acid nomenclature used here is equivalent to the alcohol "beta" carbon in Table 1.

"Hydroformylating" or "hydroformylation" is the process of reacting a compound having at least one carbon-carbon double bond (an olefin) in an atmosphere of carbon monoxide and hydrogen over a cobalt or rhodium catalyst, which results in addition of at least one aldehyde moiety to the underlying compound. U.S. Pat. No. 6,482,972, which is incorporated herein by reference in its entirety, describes the hydroformylation (oxo) process.

"Hydrogenating" or "hydrogenation" is addition of hydrogen ($H_2$) to a double-bonded functional site of a molecule, such as in the present case, addition of hydrogen to the aldehyde moieties of a di-aldehyde, to form the corresponding di-alcohol. Conditions for hydrogenation of an aldehyde are well known in the art and include, but are not limited to temperatures of 0-300° C., pressures of 1-500 atmospheres, and the presence of homogeneous or heterogeneous hydrogenation catalysts such as Pt/C, Pt/$Al_2O_3$ or Pd/$Al_2O_3$.

"Oxidizing" or "oxidation" is addition of at least one oxygen atom to organic compound, such as in the present case, addition of an oxygen atom to the aldehyde moieties of a di-aldehyde to form the corresponding di-carboxylic acid. Oxygen for the reaction can be provided by air or oxygen-enriched air. Conditions for oxidation of an aldehyde are well-known in the art, and include, but are not limited to temperatures of 0-300° C., pressures of 1-500 atmospheres, and the presence or absence of homogeneous or heterogeneous oxidation catalysts such as transition metals.

"Hydrolyzing" or "hydrolysis" is addition of water ($H_2O$) to a molecule by breaking the water molecule into H and OH groups, and adding each of those groups onto the molecule, such as in the present application wherein styrene epoxide is hydrolyzed to form phenyl-1,2-ethanediol.

"Dimerizing" or "dimerization" is co-reaction of two identical or non-identical molecules (or monomers) to form a larger molecule. Dimerization conditions are well-known in the art and include, but are not limited to, the Diels-Alder reaction, temperatures of 0-300° C., pressures of 1-500 atmospheres, and the presence of homogeneous or heterogeneous dimerization catalysts such as acid or organometallic catalysis.

"Esterifying" or "esterification" is reaction of a carboxylic acid moiety with an organic alcohol moiety to form an ester linkage. Esterification conditions are well known in the art and include, but are not limited to, temperatures of 0-300° C., and the presence or absence of homogeneous or heterogeneous esterification catalysts such as Lewis or Brønsted acid catalysts.

This disclosure is related to a potential route to non-phthalate plasticizers using light di-olefins (butadiene, dicyclopentadiene). Higher cyclic di-olefin products can be made from dimerization of light di-olefins via the Diels-Alder reaction. Hydroformylation of these higher cyclic di-olefins results in the formation of di-aldehydes. These di-aldehydes can be hydrogenated to diols or oxidized to diacids. The products of the hydrogenation or oxidation reactions are esterified with either oxo-alcohols or oxo-acids to form esters.

As discussed above, the resulting $C_6$ to $C_9$ acids or alcohols can be used individually, or together in acid mixtures or alcohol mixtures having different chain lengths, to make mixed carbon number esters to be used as plasticizers. This mixing of carbon numbers and levels of branching can be advantageous to achieve the desired compatibility with PVC for the respective polyol or polyacid used for the polar moiety end of the plasticizer, and to meet other plasticizer performance properties. The $C_6$ to $C_9$ oxo-acids or oxo-alcohols have an average branching of from about 0.2 to about 3.0 branches per molecule. Average branching is determined by NMR. The average branching of the alkyl groups incorporated into the esters as the residues of the acid or alcohol reagents ranges from about 0.2 to about 3.0 branches per residue. The starting olefin feed can be $C_3$=, butenes, $C_5$=, $C_6$=, $C_7$=, or $C_8$=.

Generally, some of the particular di-ester plasticizers of the present application can be formed by providing a di-olefin compound of the formula (IV):

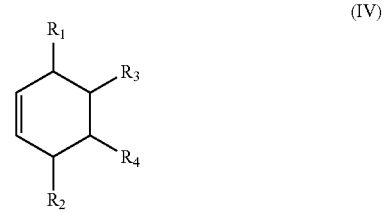

(IV)

wherein $R^1$ and $R^2$ each of which can be hydrogen, or can be joined to form a single methylene group, —$CH_2$—, and $R^3$ and $R^4$, wherein one is hydrogen and the other is —CH=$CH_2$, or can be joined to form —$CH_2$—CH=CH—, and if both $R^1$ and $R^2$ are hydrogen then one of $R^3$ or $R^4$ is —CH=$CH_2$, hydroformylating the di-olefin to form a di-aldehyde, oxidizing the di-aldehyde to form a di-acid, or alternatively hydrogenating the di-aldehyde to form a di-alcohol (diol), and subsequently esterifying the di-acid or di-alcohol with an oxo-alcohol or oxo-acid, respectively.

The oxo-diesters described above can be formed by varying placements of ester groups with respect to the olefinic groups of 4-ethenyl cyclohexene:

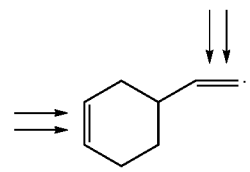

In one embodiment, a suitable di-ester of the formula:

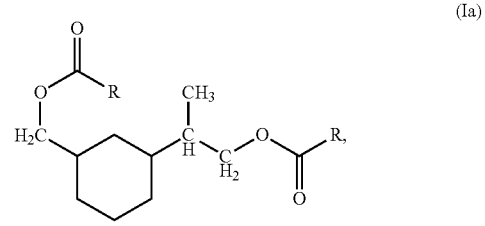

(Ia)

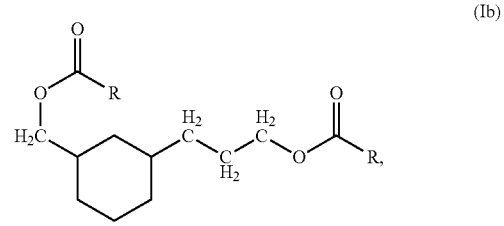

(Ib)

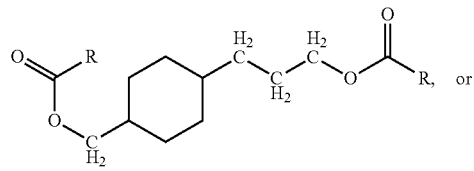
(Ic)

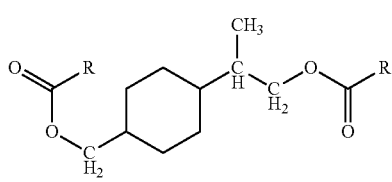
(Id)

or combinations thereof, wherein each R is the same or different and represents a $C_5$-$C_8$ alkyl group, or mixtures of $C_5$-$C_8$ alkyl groups, is formed by esterifying a diol or mixtures of diols of cyclohexane having the formula:

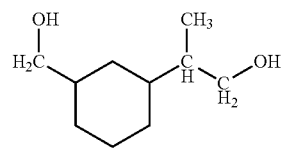
(XIIa)

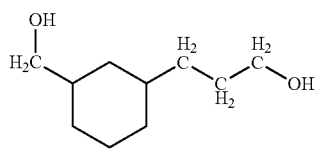
(XIIb)

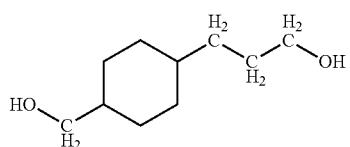
(XIIc)

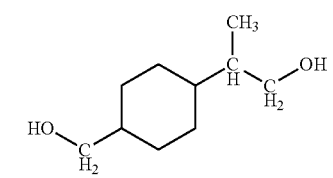
(XIId)

with $C_6$ to $C_9$ oxo-acids. In this case, the resulting R groups of formulae (Ia)-(Id) are each a $C_5$-$C_8$ alkyl group, or mixtures of $C_5$-$C_8$ alkyl groups, i.e. the alkyl residues of the $C_6$-$C_9$ oxo-acid reactants.

In an alternative embodiment, a suitable di-ester of the formula:

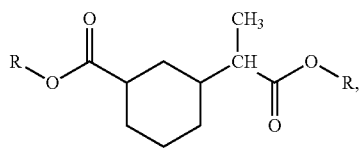
(IIa)

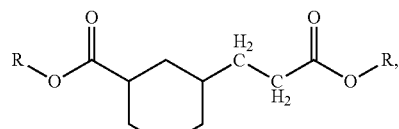
(IIb)

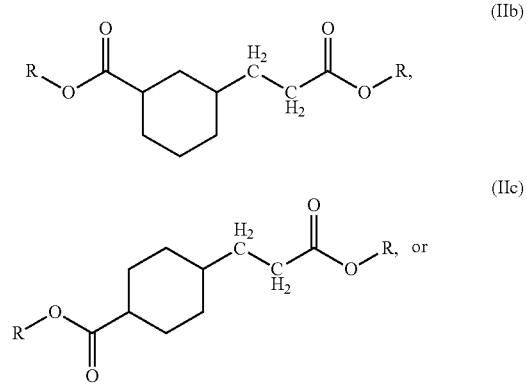
(IIc)

(IId)

or combinations thereof, wherein each R is the same or different and represents a $C_6$-$C_9$ alkyl group, or mixtures of $C_6$-$C_9$ alkyl groups, is formed by esterifying a diacid or mixtures of diacids of cyclohexane having the formula:

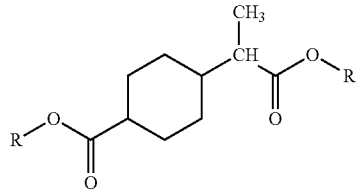
(XIIIa)

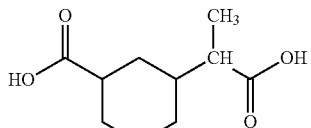
(XIIIb)

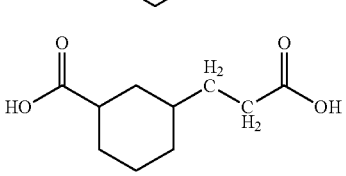
(XIIIc)

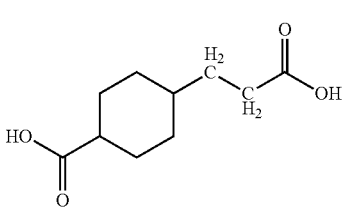
(XIIId)

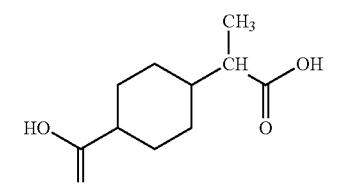

with $C_6$ to $C_9$ oxo-alcohols. In this case, the resulting R groups of formulae (IIa)-(IId) are each a $C_6$-$C_9$ alkyl group, or mixtures of $C_6$-$C_9$ alkyl groups, i.e. the alkyl residues of the $C_6$-$C_9$ oxo-alcohol reactants.

The cyclohexane oxo-diester can be formed by dimerizing 1,3-butadiene via the Diels-Alder reaction to form 4-ethenyl-cyclohexene of the formula:

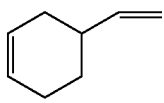

which is subsequently hydroformylated in the presence of $H_2/CO$ over a hydroformylation catalyst, such as a cobalt or rhodium compound, to form a dialdehyde or mixture of dialdehydes of the formula:

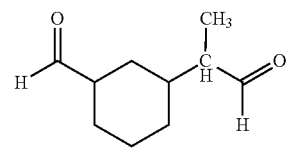
(IIIa)

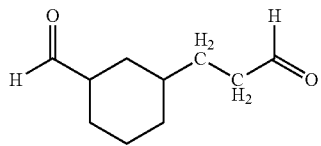
(IIIb)

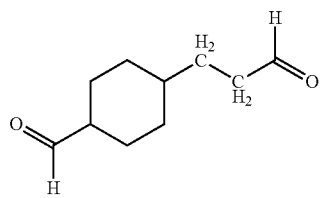
(IIIc)

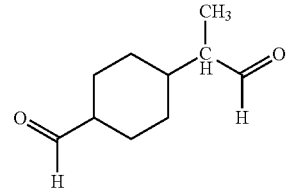
(IIId)

which is subsequently oxidized to form the diacid or hydrogenated to form the diol, which are subsequently esterified with an oxo-alcohol or an oxo-acid, respectively.

In an alternative, suitable isomeric oxo-diester plasticizers can formed by varying placements of the ester groups with respect to the olefinic carbons of dicyclopentadiene:

Such suitable plasticizers are di-esters of the formulas:

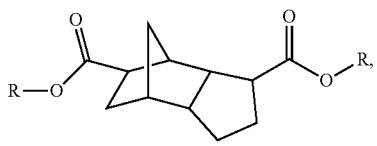
(Va)

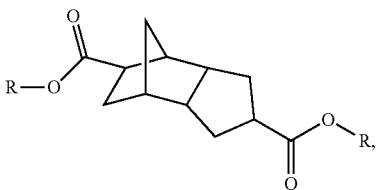
(Vb)

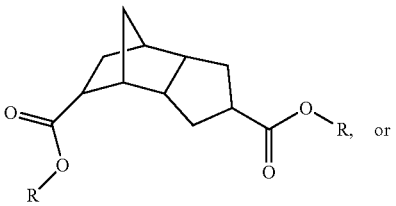
(Vc)

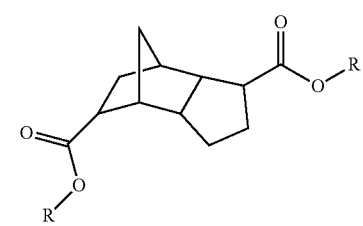
(Vd)

or combinations thereof, wherein each R is the same or different and represents a $C_6$-$C_9$ alkyl group, or mixtures of $C_6$-$C_9$ alkyl groups; or di-esters of the formulas:

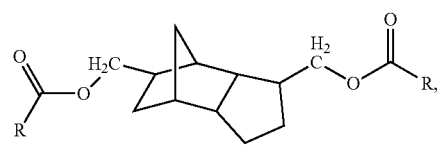
(VIa)

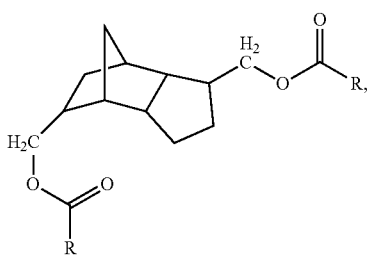
(VIb)

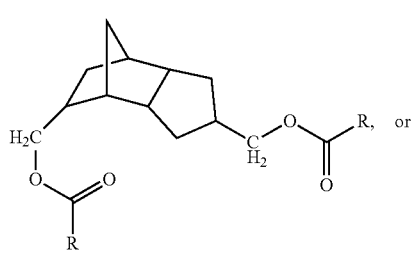
(VIc)

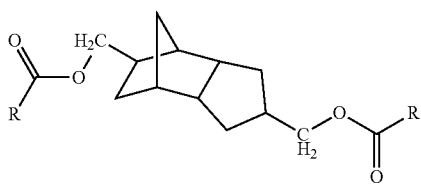

(VId)

or combinations thereof, wherein each R is the same or different and represents a $C_5$-$C_8$ alkyl group, or mixtures of $C_5$-$C_8$ alkyl groups, which are prepared starting with the dimer of cyclopentadiene, having the formula:

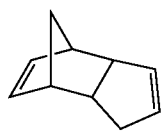

and following the hydroformylation, oxidation or hydrogenation, and esterification steps as set forth above.

We have found that when $C_6$ to $C_9$ oxo-alcohols or oxo-acids are used as reactants for the esterification reactions described above, the resulting di-esters are in the form of relatively high-boiling liquids (having low volatility), which are readily incorporated into polymer formulations as plasticizers.

In another embodiment, plasticizers of the formula

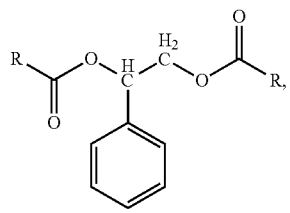

(VII)

wherein each R is the same or different and represents a $C_5$-$C_8$ alkyl group, or mixtures of $C_5$-$C_8$ alkyl groups, can be made by dimerizing 1,3-butadiene to form 4-ethenyl-cyclohexene; dehydrogenating said 4-ethenyl-cyclohexene to form styrene; oxidizing said styrene to form styrene epoxide; optionally hydrolyzing said styrene epoxide to form phenyl-1,2-ethanediol; and esterifying either of said styrene epoxide or phenyl-1,2-ethanediol with a $C_6$-$C_9$ oxo-acid.

Similarly, the oxo-diester plasticizers of the present disclosure can be formed by epoxidizing either dicyclopentadiene of the formula

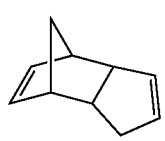

or 4-ethenyl-cyclohexene of the formula:

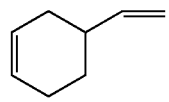

, optionally followed by hydrolyzing to form the corresponding diols or polyols, and esterification with oxo-acids. Several options are considered:

i) epoxidation of the diene to monoepoxide, followed by hydrogenation of the remaining C—C double bond, then either hydrolysis of the epoxide to diol followed by esterification with acids to the oxo-diesters, or direct esterification of the epoxide with acids to the oxo-diesters, or ii) epoxidation of the diene to diepoxide, then either followed by hydrolysis of the diepoxide to tetraol (or diol monoepoxide) followed by esterification with acids to the tetraesters, or direct esterification of the diepoxide with acids to the tetraesters, or iii) selective hydrogenation of diene to mono-olefin followed by epoxidation, then either hydrolysis of the epoxide to diol followed by esterification of the epoxide with acids, or direct esterification of the epoxide with acids to the oxo-diesters.

The oxo-diester plasticizers of the present application find use in a number of different polymers, such as vinyl chloride resins, polyesters, polyurethanes, ethylene-vinyl acetate copolymers, rubbers, poly(meth)acrylics and mixtures thereof.

EXAMPLES

General Procedure for Esterification

Into a four necked 1000 mL round bottom flask equipped with an air stirrer, nitrogen inductor, thermometer, Dean-Stark trap and chilled water cooled condenser, the appropriate diols and acids were added. The acids used may be a mixture of acids having n and m carbons (n and m may the same or different and may be linear or branched). The Dean-Stark trap was filled with the lighter boiling acid to maintain the same molar ratio of acids in the reaction flask. The reaction mixture was heated to 220° C. with air stirring under a nitrogen sweep. The water collected in the Dean-Stark trap was drained frequently. Gas chromatography analysis on the products was conducted using a Hewlett-Packard 5890 GC equipped with a HP6890 autosampler, a HP flame-ionization detector, and a J&W Scientific DB-1 30 meter column (0.32 micrometer inner diameter, 1 micron film thickness, 100% dimethylpolysiloxane coating). The initial oven temperature was 60° C.; injector temperature 290° C.; detector temperature 300° C.; the temperature ramp rate from 60 to 300° C. was 10° C./minute with a hold at 300° C. for 14 minutes. The calculated %'s reported for products were obtained from peak area, with an FID detector uncorrected for response factors.

Example 1

Esterification of phenyl-1,2-ethanediol with $C_7$ oxo-acid

Phenyl-1,2-ethanediol (100 grams, 0.724 mole) from Aldrich Chemical Co. and heptanoic acids (oxo-$C_7$ isomeric mixture) (282.8 grams, 2.17 mole) were added to the round bottom flask. Additional heptanoic acids (15.5 grams, 0.119 mole) were added to the Dean-Stark trap. The reaction mixture was heated to 220° C. with air stirring under a nitrogen sweep. The water collected in the Dean-Stark trap was drained frequently. After 6 hours heating 92% conversion was achieved based on the water collected. Liquid samples of the reaction mixture were removed periodically and analyzed for conversion, see FIG. 1. The reaction mixture was transferred to a 1 liter distillation flask and the product was fractionally distilled using an 18" Vigreaux column, air cooled condenser, multiple receiving adapter and a dry ice cooled trap. Two of the cleanest distillate cuts were combined, stirred with 1 wt % decolorizing carbon at room temperature for 2 hours, and filtered. The product distilled at 155-165° C./0.10 mm Hg vacuum and was 99.87% pure oxo-diester by GC analysis.

Example 2

Esterification of phenyl-1,2-ethanediol with $C_9$ oxo-acid

The same procedure as Example 1 was employed with a $C_9$ oxo-acid. The reactants for this example were phenyl-1,2-ethanediol (101 grams, 0.731 mole) from Aldrich Chemical Co. and nonanoic acids (oxo-$C_9$ isomeric mixture) (347.1 grams, 2.19 mole). Additional nonanoic acids (16.7 grams, 0.106 mole) were added to the Dean-Stark trap. Liquid samples of the reaction mixture were removed periodically and analyzed for conversion, see FIG. 1. After 6 hours heating, 92.14% conversion was achieved based on the water collected. The reaction mixture was transferred to a 1 liter distillation flask and the product was fractionally distilled using a Claisen adapter, air cooled condenser, multiple receiving adapter and a dry ice cooled trap. Four of the cleanest distillate cuts were combined. The product was 99.7% pure oxo-diester by GC analysis.

Example 3

Esterification of phenyl-1,2-ethanediol with $C_{10}$ oxo-acid

The same procedure as Example 1 was employed with a $C_{10}$ oxo-acid. The reactants for this example were phenyl-1,2-ethanediol (101 grams, 0.731 mole) from Aldrich Chemical Co. and decanoic acids (oxo-$C_{10}$ isomeric mixture) (377.0 grams, 2.19 mole). No decanoic acids were added to the Dean-Stark trap. Liquid samples of the reaction mixture were removed periodically and analyzed for conversion, see FIG. 1. After 6 hours heating 94.7% conversion was observed based on the water collected in the Dean-Stark trap. For this example the product itself was not distilled, but the excess acids were removed by distillation from the product using a Claisen adapter, air cooled condenser, receiving flask, and dry ice cooled trap. The residual product was a solid. The product was 99.9% pure oxo-diester by GC analysis with 0.1% residual acids.

Example 4

Figure 2:
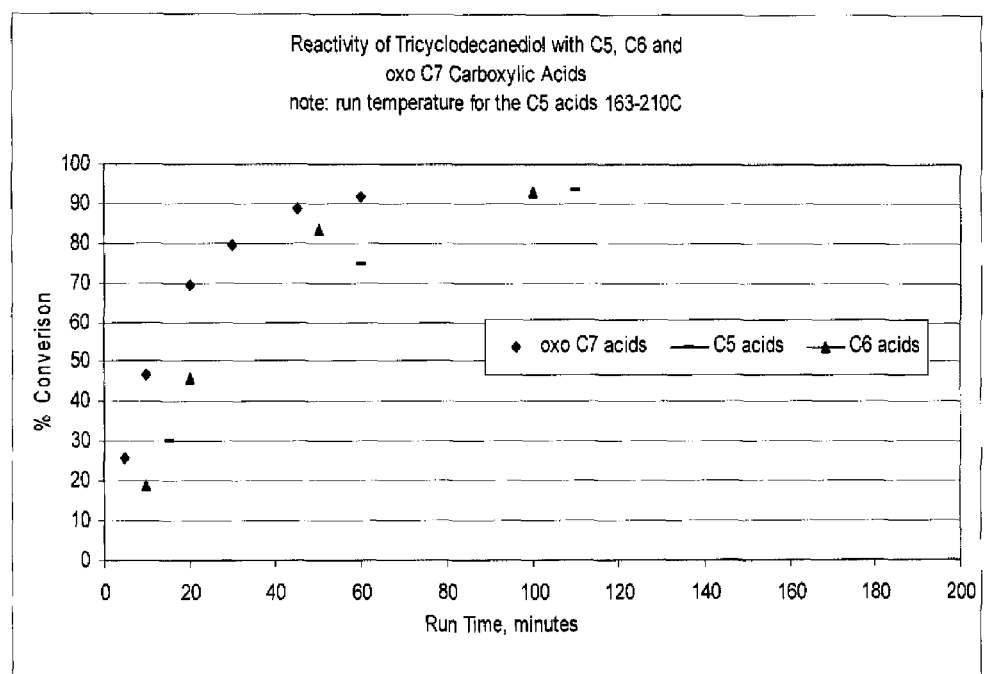
FIG. 2 is a graph indicating the reaction rates of tricyclodecanediol esterification with $C_5$ and $C_6$ acids as compared to oxo-$C_7$ acids as described in Examples 4-6.

Esterification of tricyclodecane diol with $C_7$ oxo-acid 4,8-Bis(hydroxymethyl)tricyclo[$5.2.1.0^{2,6}$]decane (isomer mixture) (147.2 grams, 0.75 mole) from Aldrich Chemical Co. and heptanoic acids (oxo-$C_7$ isomeric mixture) (293.1 grams, 2.25 mole) were added to the round bottom flask. Additional heptanoic acids (15.5 grams, 0.119 mole) were added to the Dean-Stark trap. The reaction mixture was heated to 220° C. with air stirring under a nitrogen sweep. The water collected in the Dean-Stark trap was drained frequently. After 7 hours heating 97% conversion was achieved based on the water collected. Liquid samples of the reaction mixture were removed periodically and analyzed for conversion, see FIG. 2. The reaction mixture was transferred to a 1 liter distillation flask and the excess acids were removed by distillation from the product using a Claisen adapter, air cooled condenser, receiving flask and dry ice cooled trap. The residual product was treated with 2 wt % charcoal (decolorizing carbon) to remove color by stirring the residual product at room temperature over the charcoal for 1 hour. The clean product was a clear yellow liquid after double filtration using a Buchner funnel and filter paper and was 99.8% pure oxo-diester by GC analysis.

Example 5

Esterification of tricyclodecane diol with Mixed $C_6$ acid (65% Linear+35% Branched)

The same procedure as Example 4 was employed with an isomeric mixture representative of $C_6$ oxo-acids. The reactants for this example were 4,8-bis(hydroxymethyl)tricyclo [$5.2.1.0^{2,6}$]decane (isomer mixture) (149.1 g, 0.7594 mole) from Aldrich Chemical Co. and a 65:35 by weight mixture of n-hexanoic acid (182.32 g, 1.57 mole)/2-methylvaleric acid (98.17 g, 0.844 mole) (both from Aldrich Chemical Co.). A 15.5 g quantity of this same mixture of n-hexanoic and 2-methylvaleric acids was also added to the Dean-Stark trap. The reaction mixture was heated at 220° C. for a total of 15 hours. Liquid samples of the reaction mixture were removed periodically and analyzed for conversion, see FIG. 2. After 3 hours heating, 92.7% conversion was achieved, based on the water collected. The reaction mixture was transferred to a distillation flask and the excess acids were removed by distillation, followed by a distillation of the product, using a Claisen Adapter under high vacuum. The clean product distilled at 191-187° C./0.12-0.10 mm Hg vacuum and was 99.9% pure oxo-diester by GC analysis.

Example 6

Esterification of tricyclodecane dial with Mixed $C_5$ acid (65% Linear+35% Branched)

The same procedure as Example 4 was employed with an isomeric mixture representative of $C_5$ oxo-acids. The reactants for this example were 4,8-bis(hydroxymethyl)tricyclo [$5.2.1.0^{2,6}$]decane (isomer mixture) (147.3 grams, 0.75 mole) from Aldrich Chemical Co. and a 65:35 by weight mixture of valeric acid (149.4 grams, 1.46 mole)/isovaleric acid (3-methylbutyric acid, 80.5 g, 0.79 mole) (both from Aldrich Chemical Co.). A 15.5 g quantity of this same mixture of valeric and isovaleric acids was added to the Dean-Stark trap. The run temperature for this experiment was 163-210° C. Liquid samples of the reaction mixture were removed periodically and analyzed for conversion, see FIG. 2. After 8 hours heating, 98.2% conversion was achieved based on the water collected. For this example the product was not distilled, but the excess acids were removed by distillation from the product using a Claisen adapter, air cooled condenser, receiving flask and dry ice cooled trap. The crude product was treated by adding 2 wt % charcoal (decolorizing carbon) to the crude residual product and stirring at room temperature for 2 hours, followed by filtration. The product was 99.6% pure oxo-diester by GC analysis with 0.36% monoester.

Example 7

Esterification of tricyclodecane diol with C$_9$ oxo-acid

The same procedure as Example 6 was employed with nonanoic acids (oxo-C$_9$ isomeric mixture). The reactants for this example were 4,8-bis(hydroxymethyl)tricyclo[5.2.1.0$^{2,6}$]decane (isomer mixture) (144.4 grams, 0.736 mole) from Aldrich Chemical Co. and nonanoic acids (Oxo-C$_9$ isomeric mixture) (349.3 grams, 2.207 mole). Nonanoic acids (15.5 g) were also added to the Dean-Stark trap. The reaction mixture was heated at 220° C. for 7 hours with sampling after 0.25, 1, 2 and 7 hours heating. After 7 hours heating, 94.3% conversion was achieved based on the water collected. For this example the product was not distilled, but the excess acids were removed by distillation from the product using a Claisen adapter, air cooled condenser, receiving flask and dry ice cooled trap. The crude product was treated by adding 2 wt % charcoal (decolorizing carbon) to the crude residual product and stirring at room temperature for 2 hours, followed by filtration. The product was 99.3% pure oxo-diester by GC analysis with the balance being monoester.

Example 8

Esterification of tricyclodecane diepoxide with Mixed C$_5$ acid (65% Linear+35% Branched)

A similar procedure to Example 5 was employed with an isomeric mixture representative of C$_5$ acids. The reactants for this example were dicyclopentadiene diepoxide (endo/exo mixture) (25 grams, 0.1523 mole) from Aldrich Chemical Co. and a 65:35 by weight mixture of valeric acid (60.65 grams, 0.594 mole)/isovaleric acid (3-methylbutyric acid, 32.65 g, 0.32 mole) (both from Aldrich Chemical Co.). An 18 g quantity of this same mixture of valeric and isovaleric acids was added to the Dean-Stark trap. The reaction mixture was heated at 170 to 197° C. for 24 hours with sampling for GC analysis after 2, 5, 7, 11, 15 and 24 hours. Water was not drained from the Dean-Stark trap. The reaction mixture was transferred to a distillation flask and the excess acids were removed by distillation, followed by a fractional distillation of the product, using a Claisen Adapter, air cooled condenser, receiving flask, and dry ice cooled trap under high vacuum. The product heart cut collected at 226-232° C./0.25 mm Hg vacuum. The product was 97.7% pure tetraester by GC analysis.

Example 9

Epoxidation of 5,6-dihydrodicyclopentadiene to (4,5-epoxy)-endo-tricyclo[5.2.1.0$^{2,6}$]decane Into a 2 liter four necked round bottom flask equipped with a mechanical stirrer, thermometer, and addition funnel, and maintained under a nitrogen purge, were added 5,6-dihydro-endo-dicyclopentadiene (TCI Chemical Co., 50 g, 0.3125 mol, having formula XIV):

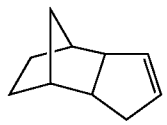

(XIV)

and 3000 mL of chloroform. The addition funnel was charged with formic acid (342.9 g, 7.45 mol). The formic acid was added dropwise over the course of 75 minutes. The dropping funnel was then charged with 30 wt % aqueous hydrogen peroxide (44.3 g, 0.39 mol). The hydrogen peroxide solution was added at 23-28° C. over a 60 minute period. The reaction mixture was stirred overnight at room temperature and subsequently extracted with 3×1000 mL of deionized water. The combined aqueous layers were extracted with chloroform (500 mL). The chloroform layers were combined and dried over magnesium sulfate and filtered. Solvent was removed using a rotary evaporator. The residual product weighed 78.9 g, with the weight above theoretical yield due to entrapped chloroform solvent (evidenced by a large protio chloroform peak in the $^1$H NMR). This procedure was repeated and the residual product of the second procedure weighed 71.8 g.

Example 10

Esterification of (4,5-epoxy)-endo-tricyclo[5.2.1.0$^{2,6}$]decane with C$_9$ oxo-acid Into a 500 mL four necked round bottom flask equipped with a thermometer, air stirrer, nitrogen inlet, Dean-Stark trap, and a reflux condenser were added (4,5-epoxy)-endo-tricyclo[5.2.1.0$^{2,6}$]decane as prepared in Example 9 (51.03 g uncorrected for purity or entrapped solvent, nominal 0.3397 mol), nonanoic acids (oxo-C$_9$ isomeric mixture) (215.65 g, 1.364 mol), and 25.4 g mixed xylenes (added to obtain sufficient reflux to remove the water by-product). Nonanoic acids were not added to the Dean-Stark trap. The reaction mixture was heated for 8 hours at 215-220° C. and the water byproduct was collected in the Dean-Stark trap. After 255 minutes heating, 86.9% conversion was achieved based on the water collected. Subsequently, the excess acids were removed and the product was distilled under vacuum. The product was collected at 175-180° C./0.10 mm Hg vacuum and was 99.8% pure by GC analysis.

Example 11

Differential Scanning Calorimetry (DSC), Viscosity, and Thermogravimetric Analysis (TGA) Property Study of Neat Esters Thermogravimetric Analysis (TGA) was conducted on the neat esters using a TA Instruments AutoTGA 2950HR instrument (25-600° C., 10° C./min, under 60 cc N$_2$/min flow through furnace and 40 cc N$_2$/min flow through balance; sample size 10-20 mg). Table 3 provides a volatility comparison of the different ester fractions. Differential Scanning Calorimetry (DSC) was also performed on the neat plasticizers, using a TA Instruments 2920 calorimeter fitted with a liquid N$_2$ cooling accessory. Samples were loaded at room temperature and cooled to about −130° C. at 10° C./min and analyzed on heating to 75° C. at a rate of 10° C./min. Table 3 provides a glass transition (T$_g$) comparison of the different ester fractions. T$_g$s given in Table 3 are midpoints of the second heats (unless only one heat cycle was performed, in which case the first heat T$_g$, which is typically in very close agreement, is given). Kinematic Viscosity (KV) was measured at 20° C. according to ASTM D-445-20, the disclosure of which is incorporated herein by reference. Comparative data for a common commercial plasticizer (diisononyl phthalate; Jayflex® (DINP), ExxonMobil Chemical Co.) is also included.

TABLE 3

Volatility, Viscosity, and Glass Transition Properties of Neat Esters.

| Ex. No. | TGA 1% Wt Loss (° C.) | TGA 5% Wt Loss (° C.) | TGA 10% Wt Loss (° C.) | TGA Wt Loss at 220° C. (%) | DSC $T_g$ (° C.) | KV (20° C., mm²/sec) |
|---|---|---|---|---|---|---|
| DINP | 184.6 | 215.2 | 228.5 | 6.4 | −79.1 | 96.81 |
| 1 | 156.1 | 186.8 | 200.7 | 24.1 | −82.7 | 30.03 |
| 2 | 176.6 | 206.9 | 221.4 | 9.2 | −75.9 | 58.07 |
| 3* | — | — | — | — | — | — |
| 4 | 191.6 | 222.7 | 238.8 | 4.4 | −78.8 | 112.61 |
| 5 | 186.2 | 216 | 231 | 6.0 | −84.5 | 63.37 |
| 6 | 173.2 | 203.9 | 218.7 | 10.5 | −82.3 | 65.48 |
| 7 | 203.9 | 236.0 | 252.2 | 2.3 | −71.4 | 208.19 |
| 8 | 190.8 | 231.4 | 247.8 | 3.0 | −53.7 | — |
| 10 | 177.8 | 212.5 | 227.7 | 7.1 | −65.3 | 210.95 |

— Data not taken.

Example 12

General Procedure for the Use of Esters to Plasticize Poly(Vinyl Chloride)

A 5.85 g portion of the ester sample (or comparative commercial plasticizer DINP) was weighed into an Erlenmeyer flask which had previously been rinsed with uninhibited tetrahydrofuran (THF) to remove dust. An 0.82 g portion of a 70:30 by weight solid mixture of powdered Drapex® 6.8 (Crompton Corp.) and Mark® 4716 (Chemtura USA Corp.) stabilizers was added along with a stirbar. The solids were dissolved in 117 mL uninhibited THF. Oxy Vinyls® 240F PVC (11.7 g) was added in powdered form and the contents of the flask were stirred overnight at room temperature until dissolution of the PVC was complete. The clear solution was poured evenly into a flat aluminum paint can lid (previously rinsed with inhibitor-free THF to remove dust) of dimensions 7.5" diameter and 0.5" depth. The lid was placed in an oven at 60° C. for 2 hours with a moderate nitrogen purge. The pan was removed from the oven and allowed to cool for a ~5 min period. The resultant clear film was carefully peeled off of the aluminum, flipped over, and placed back evenly into the pan. The pan was then placed in a vacuum oven at 70° C. overnight to remove residual THF. The dry, flexible, typically almost colorless film was carefully peeled away and exhibited no oiliness or inhomogeneity unless otherwise noted. The film was cut into small pieces to be used for preparation of test bars by compression molding (size of pieces was similar to the hole dimensions of the mold plate). The film pieces were stacked into the holes of a multi-hole steel mold plate, preheated to 170° C., having hole dimensions 20 mm×12.8 mm×1.8 mm (ASTM D1693-95 dimensions). The mold plate was pressed in a PHI company QL-433-6-M2 model hydraulic press equipped with separate heating and cooling platforms. The upper and lower press plates were covered in Teflon™-coated aluminum foil and the following multistage press procedure was used at 170° C. with no release between stages: (1) 3 minutes with 1-2 ton overpressure; (2) 1 minute at 10 tons; (3) 1 minute at 15 tons; (4) 3 minutes at 30 tons; (5) release and 3 minutes in the cooling stage of the press (7° C.) at 30 tons. A knockout tool was then used to remove the sample bars with minimal flexion. Typically near-colorless, flexible bars were obtained which, when stored at room temperature, showed no oiliness or exudation several weeks after pressing unless otherwise noted.

Example 13

Figure 3:
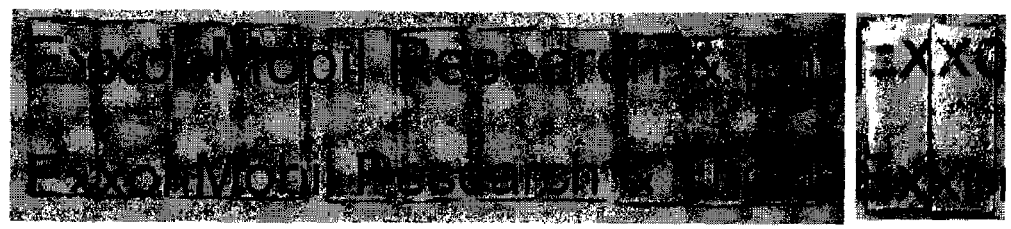
FIG. 3 is a picture of plasticized PVC test bars described in Example 13 containing the esters of the present disclosure and those of the prior art (see Example 13 for legend).

Properties of PVC Bars Plasticized with Esters Versus PVC Bars Plasticized with Commercial Plasticizer Two each of the sample bars prepared in Example 12 were visually evaluated for appearance and clarity and further compared to identically prepared bars plasticized with DINP by placing the bars over a standard printed text. The qualitative and relative flexibility of the bars was also crudely evaluated by hand. The various bars were evaluated in different test batches; thus, a new DINP control bar was included with each batch. The bars were placed in aluminum pans which were then placed inside a glass crystallization dish covered with a watch glass. The bars were allowed to sit under ambient conditions at room temperature for at least three weeks and re-evaluated during and/or at the end of this aging period. Table 4 presents appearance rankings and notes for the ester-containing bars and the control DINP-containing bars. FIG. 3 is a photograph of the test bars prepared with the esters of Examples 1, 2, 4-8, and 10, and the comparative commercial plasticizer DINP (DINP comparatives for Examples 1, 2, 4-8, 4 left bars; DINP comparative for Example 10, second bar from right). (The test bar containing the plasticizer of Example 2 had developed some oiliness at the time the photo was taken, almost 6 months after pressing).

TABLE 4

Initial and Room Temperature Aging Clarity and Appearance Properties of Ester-Containing PVC Bars and DINP-Containing PVC Control Bars.

| Example No. (Plasticizer Used in Bar) | Initial Clarity Value* | Final Clarity Value (day of evaluation) | Notes on Bar |
|---|---|---|---|
| 1 | 1[a] | 1 (29) | Not recorded |
| 2 | 1 | 1 (21) | Not recorded[c] |
| 4 | 1 | 1 (21) | Not recorded |
| 5 | 1[b] | 1 (32) | Excellent flex, better than DINP |
| 6 | 1[b] | 1 (32) | Excellent flex, better than DINP |
| 7 | 1 | 1 (35) | Low flex, not quite stiff |
| 8 | 1[a] | 1 (29) | Stiff (day 29) |
| 10 | —[d] | 1 (26) | Oily at Day 26, very stiff |
| DINP ctrl for 1, 8 | 1[a] | 1 (29) | Not recorded |
| DINP ctrl for 2, 4 | 1 | 1 (21) | Not recorded |
| DINP ctrl for 5, 6 | 1[b] | 1 (32) | Not recorded |
| DINP ctrl for 7 | 1 | 1 (35) | Moderate flex |
| DINP ctrl for 10 | — | 1 (26) | Somewhat stiff |

*1-5 scale, 1 = no distortion, 5 = completely opaque.
— Data not taken. No bars exhibited oiliness, stickiness, or inhomogeneity unless noted.
[a]Evaluated 3 days after pressing.
[b]Evaluated 2 days after pressing.
[c]This bar had developed some oiliness at the time the photo of FIG. 3 was taken, almost 6 months after pressing, but was not oily upon initial pressing or during the evaluation period. No other bars except for the Example 10 bar exhibited oiliness at the time the photo was taken.
[d]This bar was not noted as oily immediately after pressing.

Example 14

98° C. Weight Loss Comparison of PVC Bars Plasticized with Esters Versus PVC Bars Plasticized with Commercial Plasticizer Two each of the PVC sample bars prepared in Example 12 were placed separately in aluminum weighing pans and placed inside a convection oven at 98° C. Initial weight measurements of the hot bars and measurements taken at specified time intervals were recorded and results were averaged between the bars. The averaged results are shown in Table 5. Notes on the appearance and flexibility of the bars at the end of the test are also given. The final color of the bars (even DINP control samples) varied between batches; gross comparisons only should be made between bars of different test batches.

of distilled water and the copper insert was adjusted so that the bottom of each bar was ~1" above the water level. The jar was sealed, placed in a 70° C. convection oven, and further sealed by winding Teflon™ tape around the edge of the lid. After 21 days the jars were removed from the oven, allowed to cool for ~20 minutes, opened, and the removed bars were allowed to sit under ambient conditions in aluminum pans (with the bars propped at an angle to allow air flow on both faces) or hanging from the copper inserts for ca. 1 week (until reversible humidity-induced opacity had disappeared). The bars were evaluated visually for clarity. All bars exhibited complete opacity during the duration of the test and for several days after removal from the oven. Results are shown in Table 6. Notes on the appearance and flexibility of the bars at the end of the test are also given.

TABLE 5

% Weight Loss at 98° C. of Ester-Containing PVC Bars and DINP-Containing PVC Control Bars.

| Example No. (Plasticizer Used in Bar) | Day 1 | Day 2 | Day 3 | Day 7 | Day 14 | Day 21 | Notes on Bar |
|---|---|---|---|---|---|---|---|
| 1 | 0.90 | 1.65 | 2.24 | 4.62 | 7.10 | 8.48 | Curled/brittle, med dark brown |
| 2 | 0.35 | 0.49 | 0.60 | 0.91 | 1.35 | 1.76 | Dark brown, brittle, some buckling |
| 4 | 0.37 | 0.48 | 0.54 | 0.70 | 0.93 | 1.10 | Very good (light color w/ yellow spots, still flexible |
| 5 | 0.28 | 0.32 | 0.39 | 0.57 | 0.77 | 0.92 | Light color, good flex. |
| 6 | 0.36 | 0.42 | 0.53 | 0.93 | 1.50 | 2.03 | Light color, OK flex. |
| 7 | 0.22 | 0.29 | 0.34 | 0.35 | 0.42 | 0.43 | Light orange color, low flex. but not brittle |
| 8 | 0.75 | 0.79 | 0.87 | 0.90 | 0.97 | 0.96 | Very brittle but light color |
| 10[a] | 0.12 | 0.13 | 0.19 | 0.22 | 0.31 | 0.39 | Medium brown, oily, stiff |
| DINP ctrl for 1, 8 | 0.26 | 0.33 | 0.40 | 0.55 | 0.73 | 0.83 | OK flex, medium brown |
| DINP ctrl for 2, 4 | 0.27 | 0.32 | 0.42 | 0.32 | 0.72 | 1.10 | Light color with yellow spots; still flexible |
| DINP ctrl for 5, 6 | 0.36 | 0.58 | 0.42 | 0.54 | 0.82 | 0.94 | Medium dark color, good flex. |
| DINP ctrl for 7 | 0.20 | 0.27 | 0.31 | 0.36 | 0.48 | 0.56 | Medium brown, good flex. |
| DINP ctrl for 10[a] | 0.18 | 0.17 | 0.16 | 0.20 | 0.23 | 0.32 | Medium brown, moderately flexible |

Bars did not exhibit oiliness, stickiness, or inhomogeneity unless noted.
[a]The samples in this batch were rotated front-to-back and left-to-right daily with other samples in the same batch, so that they experienced more even heating in the oven.

Example 15

70° C. Humid Aging Clarity Comparison of PVC Bars Plasticized with Esters Versus PVC Bars Plasticized with Commercial Plasticizer Using a standard one-hole office paper hole punch, holes were punched in two each of the sample bars prepared in Example 12 about ⅛" from one end of the bar. The bars were hung in a glass pint jar (2 bars per jar) fitted with a copper insert providing a stand and hook. The jar was filled with ~½"

TABLE 6

70° C. Humid Aging Clarity and Appearance Properties of Ester-Containing PVC Bars and DINP-Containing PVC Control Bars.

| Example No. (Plasticizer Used in Bar) | Clarity Value After Test (days aged at ambient) | Notes on Bar |
|---|---|---|
| 1 | 1.5 (10) | Good flexibility |
| 2 | 2 (10) | None recorded |
| 4 | 1.5 (10) | Oily/brittle, fingerprints show on bar |
| 5 | 1 (11) | Good flexibility |
| 6 | 1 (11) | Good flexibility |

TABLE 6-continued

70° C. Humid Aging Clarity and Appearance Properties of Ester-Containing PVC Bars and DINP-Containing PVC Control Bars.

| Example No. (Plasticizer Used in Bar) | Clarity Value After Test (days aged at ambient) | Notes on Bar |
|---|---|---|
| 7 | 1.5 (14) | Low/mod flex, sl. sticky no fingerprints |
| 8 | 1.5 (10) | Completely brittle |
| 10[a] | 2 (20) | Brittle, oily |
| DINP ctrl for 1, 8 | 1.5 (10) | Still very flexible |
| DINP ctrl for 2, 4 | 1 (10) | Very flexible |
| DINP ctrl for 5, 6 | 1.5 (11) | Good flexibility |
| DINP ctrl for 7 | 1 (14) | Moderate flexibility |
| DINP ctrl for 10[a] | 1.5 (20) | OK, good flexibility |

*1-5 scale, 1 = no distortion, 5 = completely opaque. Bars did not exhibit oiliness, stickiness, or inhomogeneity unless noted.
[a]The samples in this batch were rotated front-to-back and left-to-right daily with other samples in the same batch, so that they experienced more even heating in the oven.

Example 16

Tables 7 and 8 Summarize the Critical Properties for Plasticizer Performance for the Esters of Examples 1-2 (Table 7) and 4-8 (Table 8)

TABLE 7

Critical Parameters for Plasticization Performance of Phenyl-1,2-ethanediol Esters.

| Ex. No. | Alcohol | Acid | KV (20° C., mm$^2$/sec) | $T_g$ (° C.) | Neat TGA % Wt. Loss, 220° C. | 98° C. % Wt. Loss of PVC Bar, 21 days |
|---|---|---|---|---|---|---|
| DINP | Oxo-C$_9$ | Phthalic anhydride | 96.81 | −79.1 | 6.4 | 0.56-1.10 |
| 1 | PED | Oxo-C$_7$ | 30.03 | −82.7 | 24.1 | 8.48 |
| 2 | PED | Oxo-C$_9$ | 58.07 | −75.9 | 9.2 | 1.76 |

PED = Phenyl-1,2-ethanediol

TABLE 8

Critical Parameters for Plasticization Performance of Dicyclopentadiene-Based Esters.

| Ex. No. | Alcohol | Acid | KV (20° C., mm$^2$/sec) | $T_g$ (° C.) | Neat TGA % Wt. Loss, 220° C. | 98° C. % Wt. Loss of PVC Bar, 21 days |
|---|---|---|---|---|---|---|
| DINP | Oxo-C$_9$ | Phthalic anhydride | 96.81 | −79.1 | 6.4 | 0.56-1.10 |
| 6 | TCD diol | C$_5$ n/iso mixture | 65.48 | −82.3 | 10.5 | 2.03 |
| 5 | TCD diol | C$_6$ n/iso mixture | 63.37 | −84.5 | 6.0 | 0.92 |
| 4 | TCD diol | Oxo-C$_7$ | 112.61 | −78.8 | 4.4 | 1.10 |
| 7 | TCD diol | Oxo-C$_9$ | 208.19 | −71.4 | 2.3 | 0.43 |
| 8 | TCD diepoxide | C$_5$ n/iso mixture | — | −53.7 | 3.0 | 0.96 |

— Not taken.
TCD diol = 4,8-bis(hydroxymethyl)tricyclo[5.2.1.0$^{2,6}$]decane (isomer mixture);
TCD diepoxide = dicyclopentadiene dioxide (endo/exo mixture).

Example 17

Further Demonstration of PVC Plasticization with oxo-C$_6$ TCD-diol Ester Plasticizer of Example 5

Plasticized PVC samples containing either the oxo-C$_6$ TCD-diol ester plasticizer of Example 5 or DINP (as a comparative) were mixed at room temperature with moderate stirring, then placed on a roll mill at 340° F. and milled for 6 minutes. The flexible vinyl sheet was removed and compression molded at 340° F. The samples had the following formulation: 100 phr Oxy Vinyls® 240 PVC resin; 50 phr oxo-ester or DINP; 2.5-3 phr epoxidized soybean oil; 2.5 phr Mark® 1221 Ca/Zn stabilizer; 0.25-0.3 phr stearic acid. Comparison of the data for the formulations is given in Table 9.

TABLE 9

Properties of PVC Plasticized With 50 phr of Oxo-C$_6$ TCD-Diol Ester (Example 5) Versus DINP

| Plasticizer Used in Formulation | Ex. 5 TCD-Diol Ester | DINP |
|---|---|---|
| Original Mechanical Properties | | |
| Shore A Hardness (15 sec.) | 76.7 | 80.3 |
| 95% Confidence Interval | 0.4 | — |
| Shore D Hardness (15 sec.) | 25.2 | — |
| 95% Confidence Interval | 0.2 | — |
| 100% Modulus Strength, psi | 1611 | 1691 |
| 95% Confidence Interval | 27 | — |

TABLE 9-continued

Properties of PVC Plasticized With 50 phr of Oxo-$C_6$ TCD-Diol Ester (Example 5) Versus DINP

| Plasticizer Used in Formulation | Ex. 5 TCD-Diol Ester | DINP |
|---|---|---|
| Ultimate Tensile Strength, psi | 3236 | 3267 |
| 95% Confidence Interval | 67 | — |
| Ultimate Elongation, % | 331 | 367 |
| 95% Confidence Interval | 16 | — |
| Aged Mechanical Properties | | |
| (7 days at 100° C., AC/hour) | | |
| | | |
| Aged 100% Modulus Strength, psi | 2898 | 2390 |
| 95% Confidence Interval | 61 | — |
| Ultimate Tensile Strength, psi | 3294 | 3013 |
| 95% Confidence Interval | 84 | — |
| Ultimate Elongation, % | 224 | 267 |
| 95% Confidence Interval | 16 | — |
| Weight Loss, Wt % | 11.6 | 7.0 |
| 95% Confidence Interval | 0.82 | — |
| Retained Properties | | |
| (7 days at 100° C., AC/hour) | | |
| | | |
| Retained 100% Modulus Strength, % | 180 | 141 |
| 95% Confidence Interval | 0.6 | — |
| Retained Tensile Strength, % | 102 | 92 |
| 95% Confidence interval | 0.3 | — |
| Retained Elongation, % | 68 | 73 |
| 95% Confidence Interval | 1.2 | — |
| Low Temperature | | |
| | | |
| Clash Berg ($T_f$), ° C. | −15.0 | −21.0 |
| 95% Confidence Interval | 0.9 | — |

— = Data unavailable.

Example 18

Weight Loss Study of Plasticized PVC Bars

A small portion of selected plasticized sample bars prepared in Example 12 were subjected to Thermogravimetric Analysis as previously described to evaluate plasticizer volatility in the formulated test bars. Results are shown in Table 10.

TABLE 10

% Weight Loss by TGA of Plasticized PVC Bars.

| Ex. No. of Material Used in Bar | TGA 1% Loss (° C.) | TGA 5% Loss (° C.) | TGA 10% Loss (° C.) | % Loss, 220° C. |
|---|---|---|---|---|
| DINP | 204.6 | 247.4 | 257.6 | 1.8 |
| 5 | 198.8 | 238.0 | 249.2 | 2.5 |

Example 19

Demonstration of PVC Plasticization by Differential Scanning Calorimetry (DSC) and Dynamic Thermal Mechanical Analysis (DMTA)

Three-point bend Dynamic Mechanical Thermal Analysis (DMTA) with a TA Instruments DMA Q980 fitted with a liquid $N_2$ cooling accessory and a three-point bend clamp assembly was used to measure the thermo-mechanical performance of neat PVC and the PVC/plasticizer blend sample bars prepared in Example 12. Samples were loaded at room temperature and cooled to −60° C. or lower at a cooling rate of 3° C./min. After equilibration, a dynamic experiment was performed at one frequency using the following conditions: 3° C./min heating rate, 1 Hz frequency, 20 micrometer amplitude, 0.01 pre-load force, force track 120%. Two or three bars of each sample were typically analyzed; numerical data was taken from the bar typically exhibiting the highest room temperature storage modulus (the bar assumed to have the fewest defects) unless another run was preferred for data quality. Glass transition onset values were obtained by extrapolation of the tan delta curve from the first deviation from linearity. The DMTA measurement gives storage modulus (elastic response modulus) and loss modulus (viscous response modulus); the ratio of loss to storage moduli at a given temperature is tan delta. The beginning (onset) of the $T_g$ (temperature of brittle-ductile transition) was obtained for each sample by extrapolating a tangent from the steep inflection of the tan delta curve and the first deviation of linearity from the baseline prior to the beginning of the peak. Table 11 provides a number of DMTA parameters for the bars (the temperature at which the storage modulus equals 100 MPa was chosen to provide an arbitrary measure of the temperature at which the PVC loses a set amount of rigidity; too much loss of rigidity may lead to processing complications for the PVC material). The flexible use temperature range of the samples was evaluated as the range between the $T_g$ onset and the temperature at which the storage modulus was 100 MPa. A lowering and broadening of the glass transition for neat PVC was observed upon addition of the OXO ester plasticizer, indicating plasticization. Plasticization (enhanced flexibility) was also demonstrated by lowering of the PVC room temperature storage modulus. Differential Scanning Calorimetry (DSC) was also performed on the compression-molded sample bars (−90° C. to 100-170° C. at 10° C./min). Small portions of the sample bars (~5-7 mg) were cut for analysis, making only vertical cuts perpendicular to the largest surface of the bar to preserve the upper and lower compression molding "skins"; the pieces were then placed in the DSC pans so that the upper and lower "skin" surfaces contacted the bottom and top of the pan. Alternately, DSC was conducted on leftover pieces of thin film. Results are summarized in Table 11; lowering and broadening of the glass transition for neat PVC indicates plasticization by the OXO-ester (for aid in calculating the numerical values of these broad transitions, the DSC curve for each plasticized bar was overlaid with the analogous DMTA curve for guidance about the proper temperature regions for the onset, midpoint, and end of $T_g$).

TABLE 11

| | | | | | | | | | |
|---|---|---|---|---|---|---|---|---|---|
| Ex. No. of Material Used in Bar | Tan Δ $T_g$ Onset (° C.) | Tan Δ Peak (° C.) | 25° C. Storage Mod. (MPa) | Temp. of 100 MPa Storage Mod. (° C.) | Flexible Use Range (° C.)[a] | DSC $T_g$ Onset (° C.) | DSC $T_g$ Midpt (° C.) | DSC $T_g$ End (° C.) | $T_m$ Max (° C.), $\Delta H_f$ (J/g)[b] |
| DINP | −37.6 | 17.1 | 48.6 | 16.9 | 54.5 | −37.8 | −24.8 | −12.2 | N/A[d] |
| 5 | −39.3 | 12.1 | 28.4 | 11.6 | 50.9 | −40.8 | −18.9 | 3.0 | 55.1, 0.75 |
| None[c] | 44.0 | 61.1 | 1433 | 57.1 | 13.1 | 44.5 | 46.4 | 48.9 | N/A |

N/A = Not analyzed.
[a]Difference between DMTA temperature of 100 MPa storage modulus and onset of $T_g$.
[b]Some sample bars showed a weak melting point ($T_m$) from the crystalline portion of PVC. Often this weak transition was not specifically analyzed, but data is given here in instances where it was recorded.
[c]Neat PVC, no plasticizer used.
[d]Very small.

Our unexpected results show that esters made from a combination of oxo-acids or oxo-alcohols with the above mentioned cyclic diacids or diols or epoxides are good plasticizers.

While the present disclosure has been described and illustrated by reference to particular embodiments, those of ordinary skill in the art will appreciate that the disclosure lends itself to variations not necessarily illustrated herein. For this reason, then, reference should be made solely to the appended claims for purposes of determining the true scope of the present disclosure.

What is claimed is:

1. Oxo-diesters of cyclohexane of the formulas:

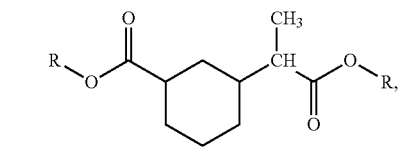
(IIa)

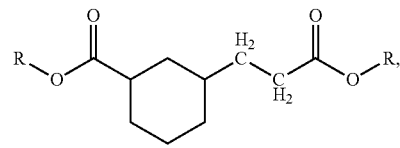
(IIb)

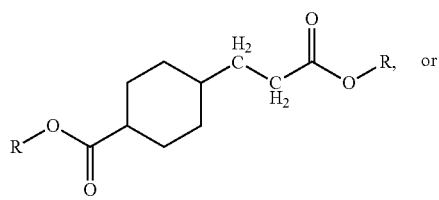
(IIc)

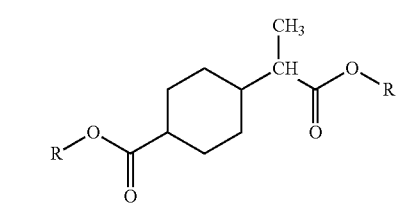
(IId)

or combinations thereof, wherein each R is the same or different and represents a $C_6$-$C_9$ alkyl group, or mixtures of $C_6$-$C_9$ alkyl groups.

2. The oxo-diesters of cyclohexane of claim 1, wherein the $C_6$-$C_9$ alkyl group, or mixtures of $C_6$-$C_9$ alkyl groups have between 0.2 and 3.0 average branches per group.

3. A process for making oxo-diesters of cyclohexane of the formula (IIa)-(IId):

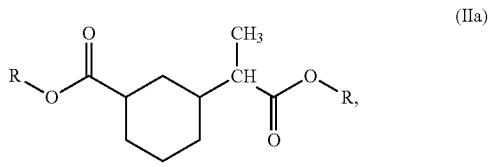
(IIa)

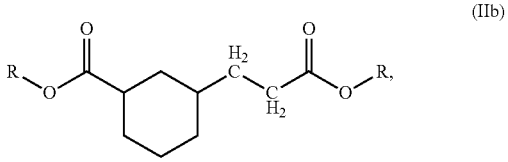
(IIb)

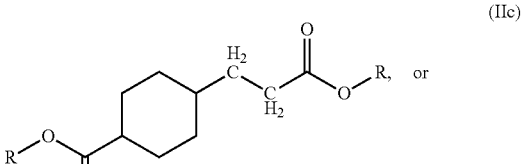
(IIc)

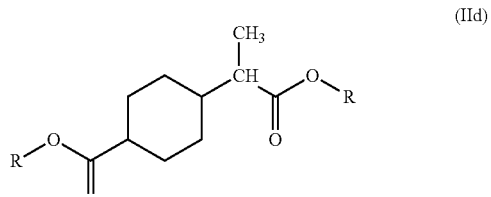
(IId)

or combinations thereof, wherein each R is the same or different and represents a $C_6$-$C_9$ alkyl group, or mixtures of $C_6$-$C_9$ alkyl groups, by dimerizing 1,3-butadiene to form 4-ethenyl-cyclohexene; hydroformylating said 4-ethenyl-cyclohexene to form a dialdehyde of cyclohexane or mixtures of dialdehydes of the formula (IIIa)-(IIId);

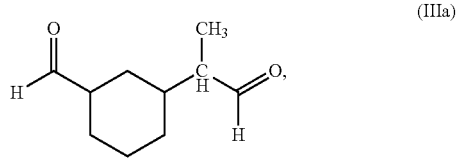
(IIIa)

-continued

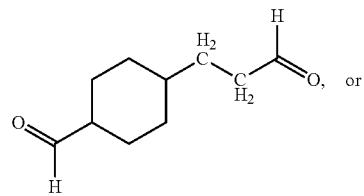
(IIIb)

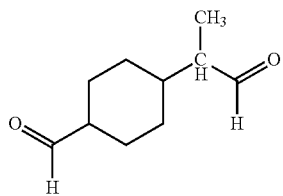
(IIIc), or

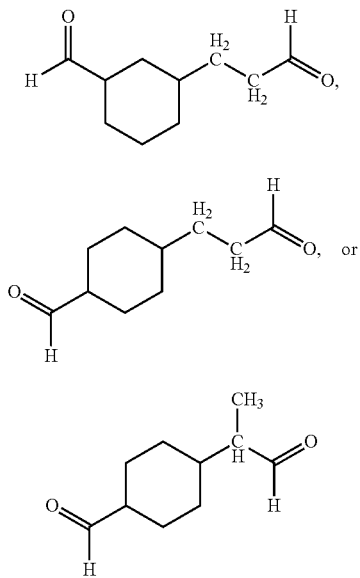
(IIId)

oxidizing said dialdehyde or mixture of dialdehydes to form the corresponding diacid of cyclohexane or mixture of diacids; and esterifying said diacid of cyclohexane or mixture of diacids with $C_6$-$C_9$ oxo-alcohols.

4. A polymer composition, comprising a polymer and one or more oxo-diesters of the following formulas (IIa)-(IId):

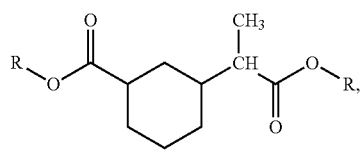
(IIa)

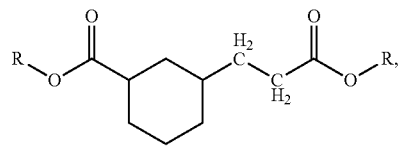
(IIb)

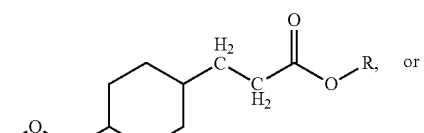
(IIc), or

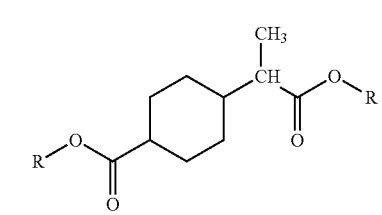
(IId)

wherein each R is the same or different and represents a $C_6$-$C_9$ alkyl group, or mixtures of $C_6$-$C_9$ alkyl groups.

5. The polymer composition of claim 4, wherein said polymer is selected from the group consisting of vinyl chloride resins, polyesters, polyurethanes, ethylene-vinyl acetate copolymers, rubbers, poly(meth)acrylics and mixtures thereof.

6. The polymer composition of claim 5, wherein said polymer is polyvinylchloride.

* * * * *